United States Patent [19]
Green et al.

[11] Patent Number: 5,620,458
[45] Date of Patent: Apr. 15, 1997

[54] SURGICAL INSTRUMENTS USEFUL FOR ENDOSCOPIC SPINAL PROCEDURES

[75] Inventors: David T. Green, Westport; Salvatore Castro, Seymour; Carlo A. Mililli, Huntington; Keith Ratcliff, Sandy Hook; Michael Castro, Seymour, all of Conn.

[73] Assignee: United States Surgical Corporation, Norwalk, Conn.

[21] Appl. No.: 213,963

[22] Filed: Mar. 16, 1994

[51] Int. Cl.$^6$ ................................................ A61B 17/00
[52] U.S. Cl. .......................... 606/198; 600/214; 600/104
[58] Field of Search ................................. 606/191, 197, 606/198, 200; 604/104–109; 600/214, 201, 204, 210

[56] References Cited

U.S. PATENT DOCUMENTS

| | | |
|---|---|---|
| Re. 33,258 | 7/1990 | Onik et al. . |
| 832,201 | 10/1906 | Kistler . |
| 1,331,737 | 2/1920 | Ylisto . |
| 1,400,648 | 12/1921 | Whitney . |
| 1,737,488 | 11/1929 | Zohlen . |
| 2,067,031 | 1/1937 | Wappler . |
| 2,137,121 | 11/1938 | Greenwald . |
| 2,689,568 | 9/1954 | Wakefield . |
| 3,486,505 | 12/1969 | Morrison . |
| 3,916,907 | 11/1975 | Peterson . |
| 4,034,746 | 7/1977 | Williams . |
| 4,168,709 | 9/1979 | Bentov ...................................... 606/198 |

(List continued on next page.)

FOREIGN PATENT DOCUMENTS

| | | |
|---|---|---|
| 77159 | 4/1983 | European Pat. Off. . |
| 38 03 342.4 | 7/1983 | Germany . |
| 57-193811 | of 1981 | Japan . |

*Primary Examiner*—Michael Powell Buiz
*Assistant Examiner*—William Lewis

[57] ABSTRACT

The present invention provides endoscopic instrumentation and surgical techniques especially useful for accessing and removing at least a portion of an intervertebral disc. Instrumentation includes tissue spreaders and cutting instruments. In particular, the tissue spreading instruments include instruments for spreading pre-sacral tissue such as fascia and for spreading adjacent vertebrae to facilitate access to the intervertebral disc. Endoscopic cutting instruments deliver a cutting blade in a sheathed position to the site of the disc nucleus followed by deployment to remove portions of the disc nucleus.

24 Claims, 21 Drawing Sheets

U.S. PATENT DOCUMENTS

| | | |
|---|---|---|
| 4,174,715 | 11/1979 | Hasson . |
| 4,190,042 | 2/1980 | Sinnreich . |
| 4,309,777 | 1/1982 | Patil . |
| 4,393,872 | 7/1983 | Reznik et al. . |
| 4,545,374 | 10/1985 | Jacobson . |
| 4,573,448 | 3/1986 | Kambin . |
| 4,573,622 | 3/1986 | Green et al. . |
| 4,654,028 | 3/1987 | Suma . |
| 4,655,219 | 4/1987 | Petruzzi . |
| 4,657,550 | 4/1987 | Daher . |
| 4,709,697 | 12/1987 | Muller . |
| 4,747,394 | 5/1988 | Watanbe . |
| 4,817,587 | 4/1989 | Janese . |
| 4,867,139 | 9/1989 | Girzadas . |
| 4,896,661 | 1/1990 | Bogert et al. . |
| 4,898,161 | 2/1990 | Grundei . |
| 4,909,789 | 3/1990 | Taguchi et al. . |
| 4,926,849 | 5/1990 | Downey . |
| 4,932,395 | 6/1990 | Mehdizadeh . |
| 4,997,432 | 3/1991 | Keller . |
| 5,000,163 | 3/1991 | Ray et al. . |
| 5,019,081 | 5/1991 | Watanabe . |
| 5,027,793 | 7/1991 | Engelhardt et al. . |
| 5,035,706 | 7/1991 | Giantureo et al. . |
| 5,059,194 | 10/1991 | Michelson . |
| 5,062,850 | 11/1991 | Mac Millan et al. . |
| 5,097,820 | 3/1992 | Shulman et al. . |
| 5,113,846 | 5/1992 | Hilterbrandt et al. . |
| 5,122,130 | 6/1992 | Keller . |
| 5,123,926 | 6/1992 | Pisharodi . |
| 5,176,129 | 1/1993 | Smith . |
| 5,192,327 | 3/1993 | Brantigan . |
| 5,195,506 | 3/1993 | Hulfish . |
| 5,195,507 | 3/1993 | Bilweis . |
| 5,213,112 | 5/1993 | Niwa et al. . |
| 5,224,954 | 7/1993 | Watts et al. . |
| 5,235,966 | 8/1993 | Jamner . |
| 5,236,460 | 8/1993 | Barber . |
| 5,242,439 | 9/1993 | Larsen et al. . |
| 5,245,987 | 9/1993 | Redmond et al. . |
| 5,246,458 | 9/1993 | Graham . |
| 5,258,005 | 11/1993 | Christian . |
| 5,261,909 | 11/1993 | Sutterlin et al. . |
| 5,271,385 | 12/1993 | Bailey ................................. 600/214 |
| 5,490,819 | 2/1996 | Nicholas et al. ................... 600/214 |

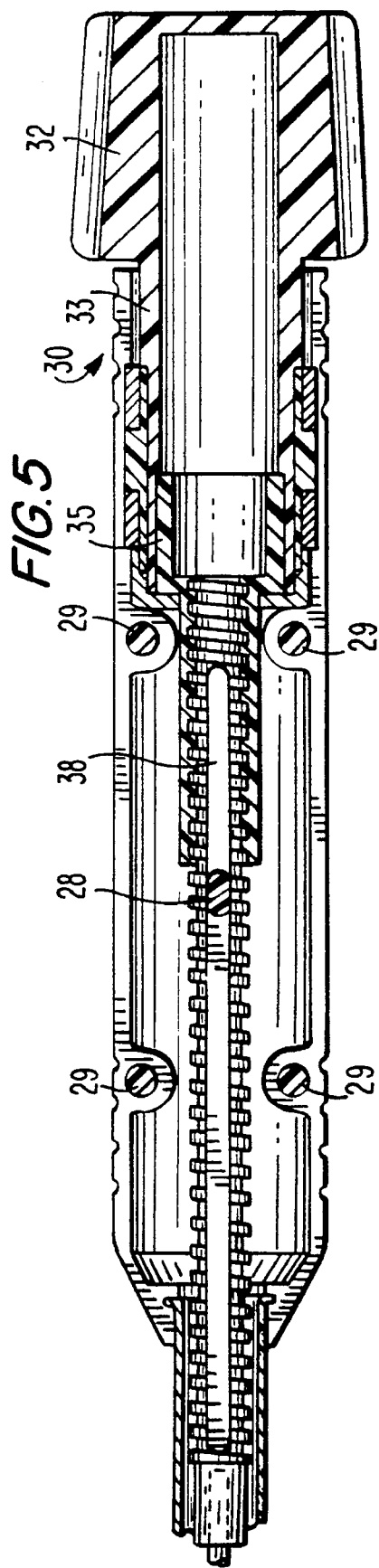
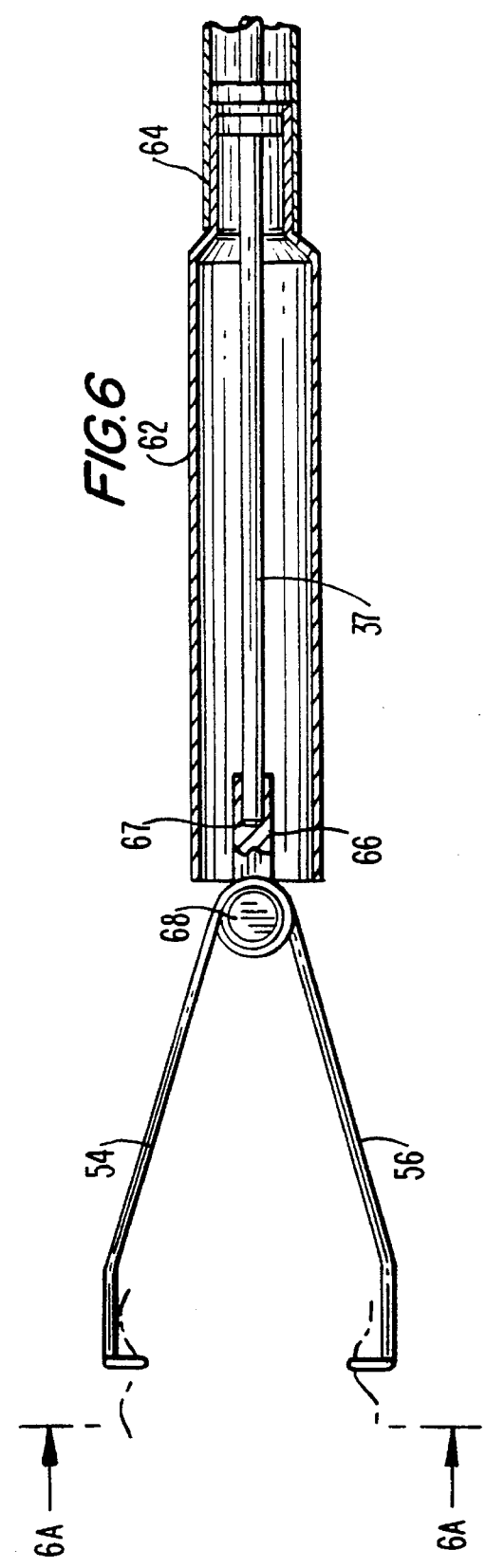
FIG.5
FIG.6

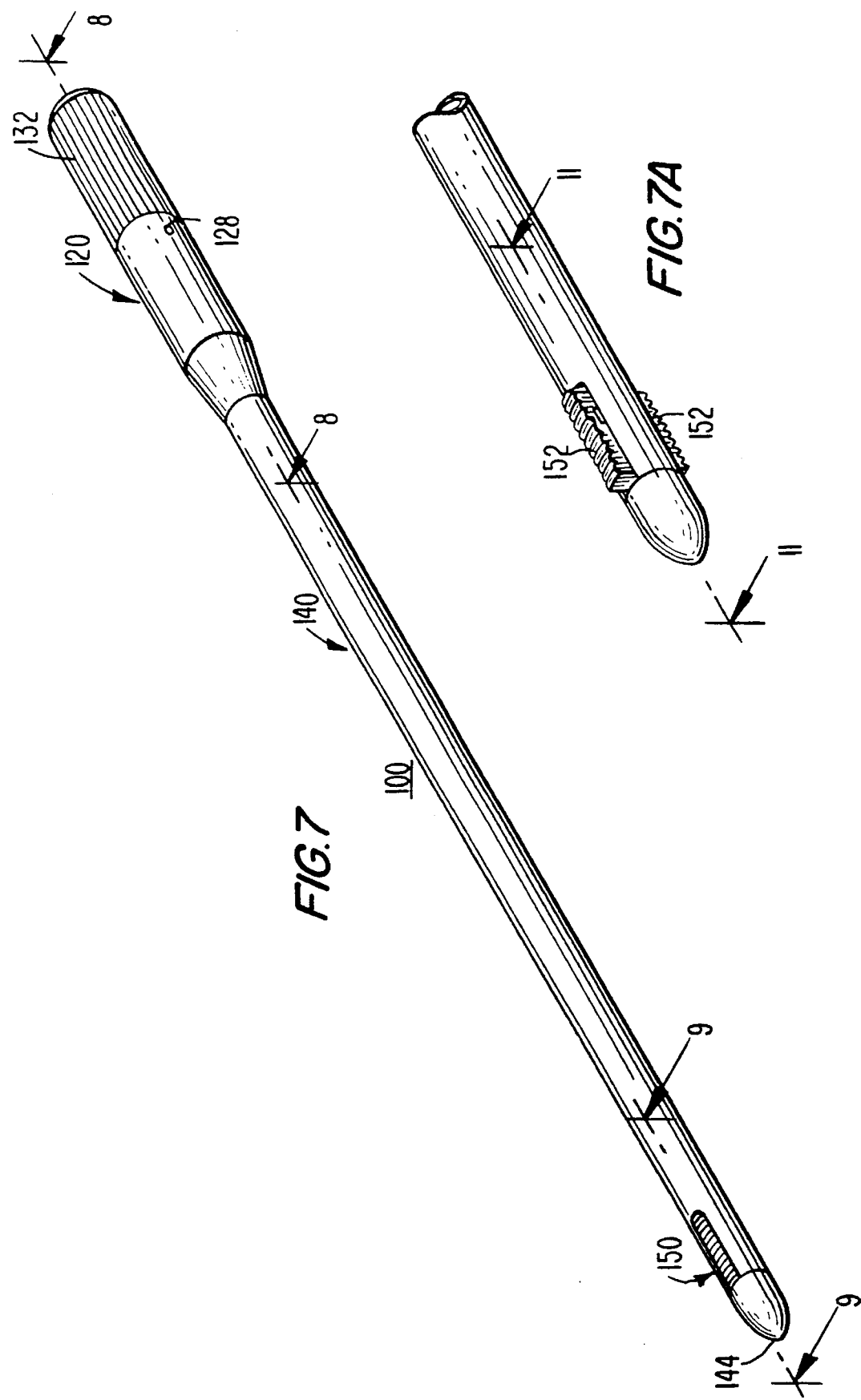

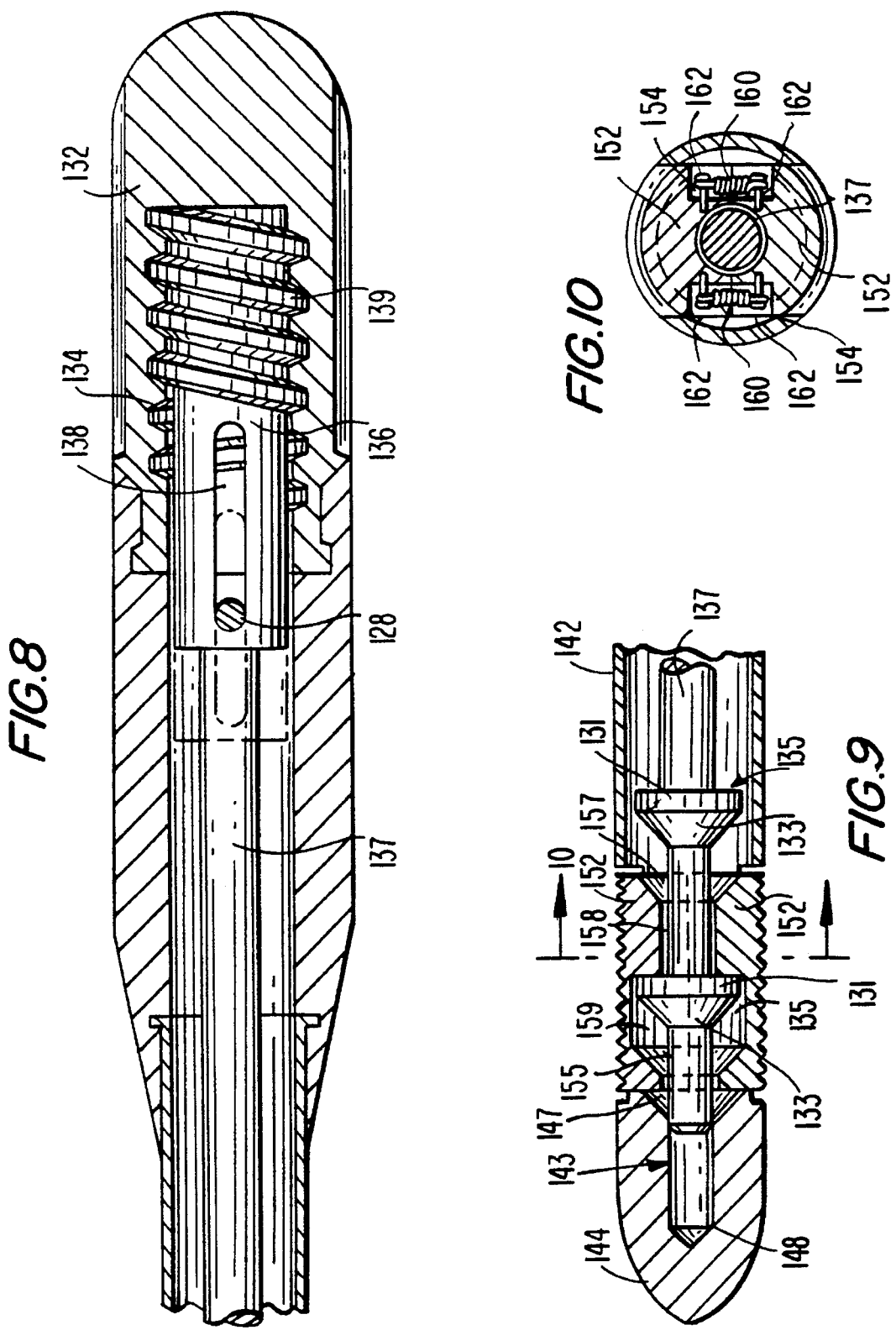

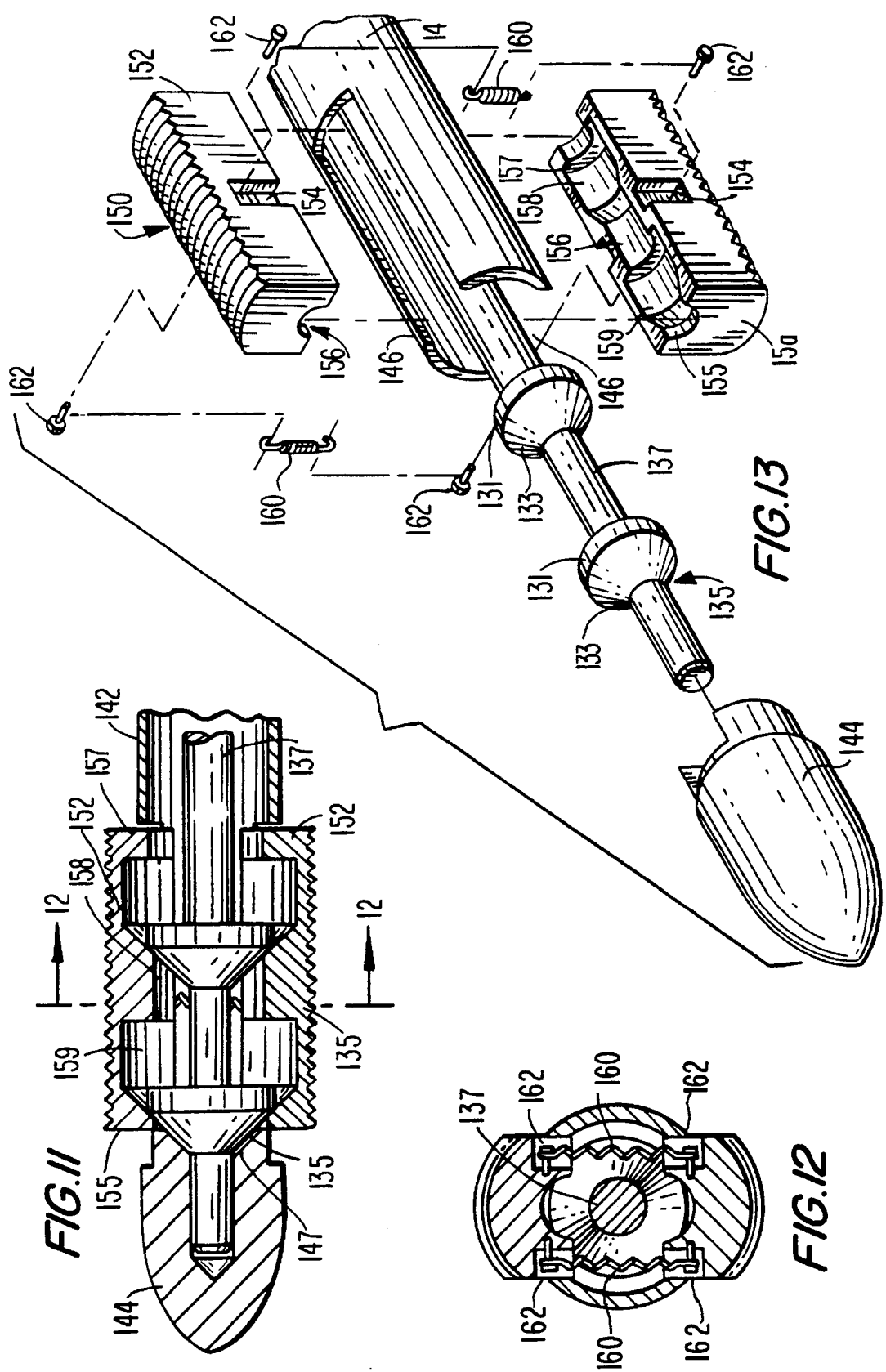

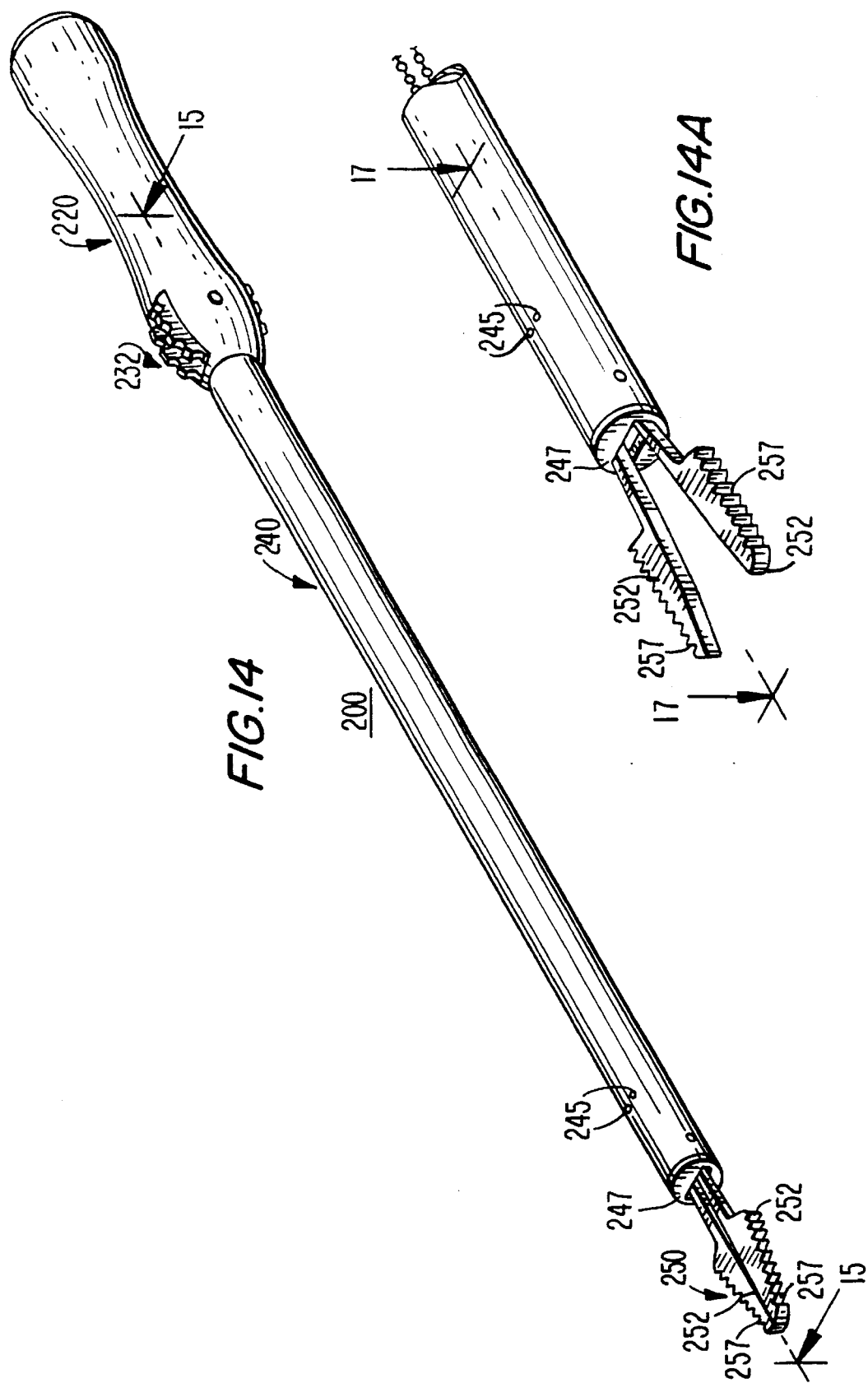

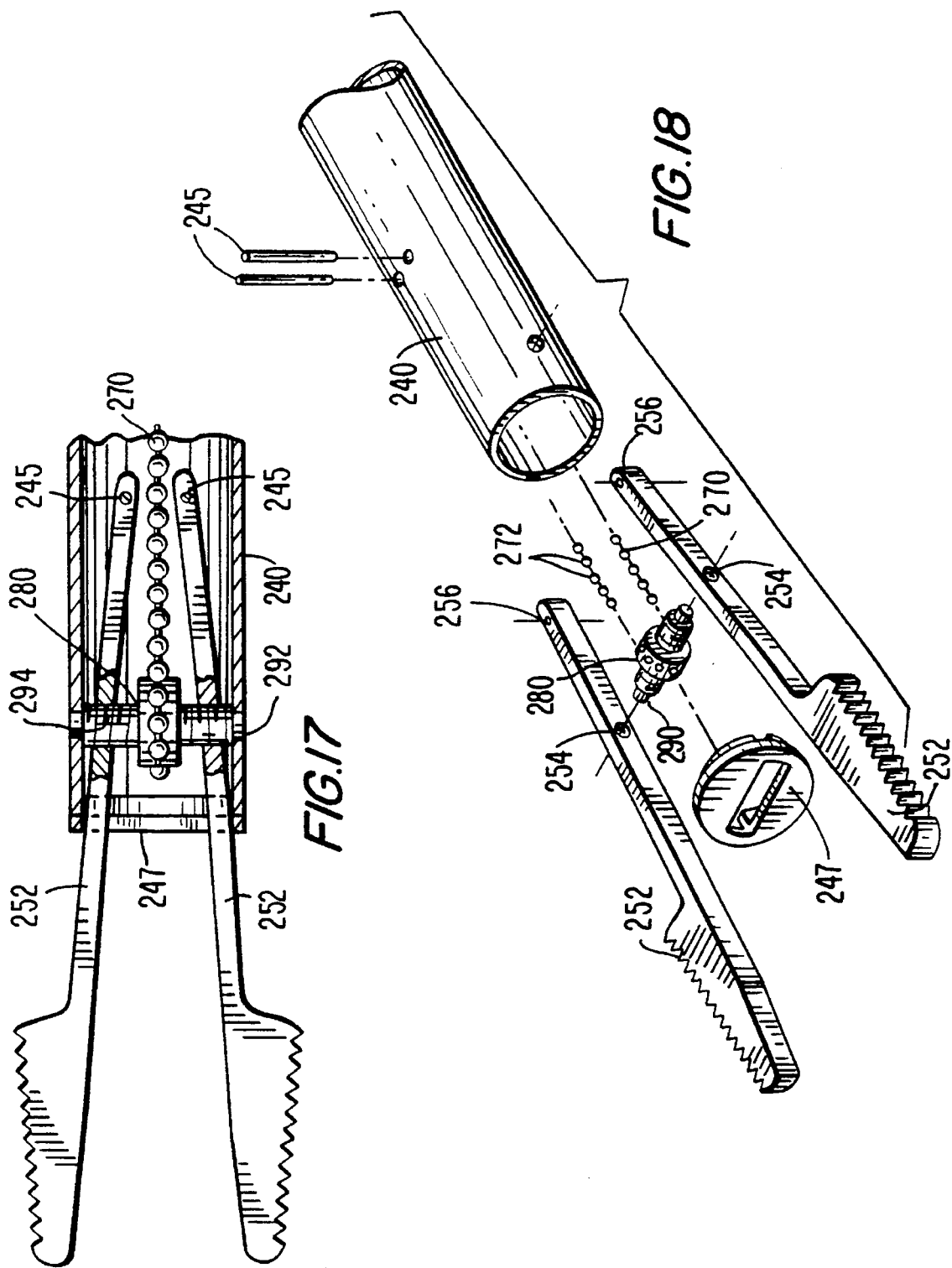

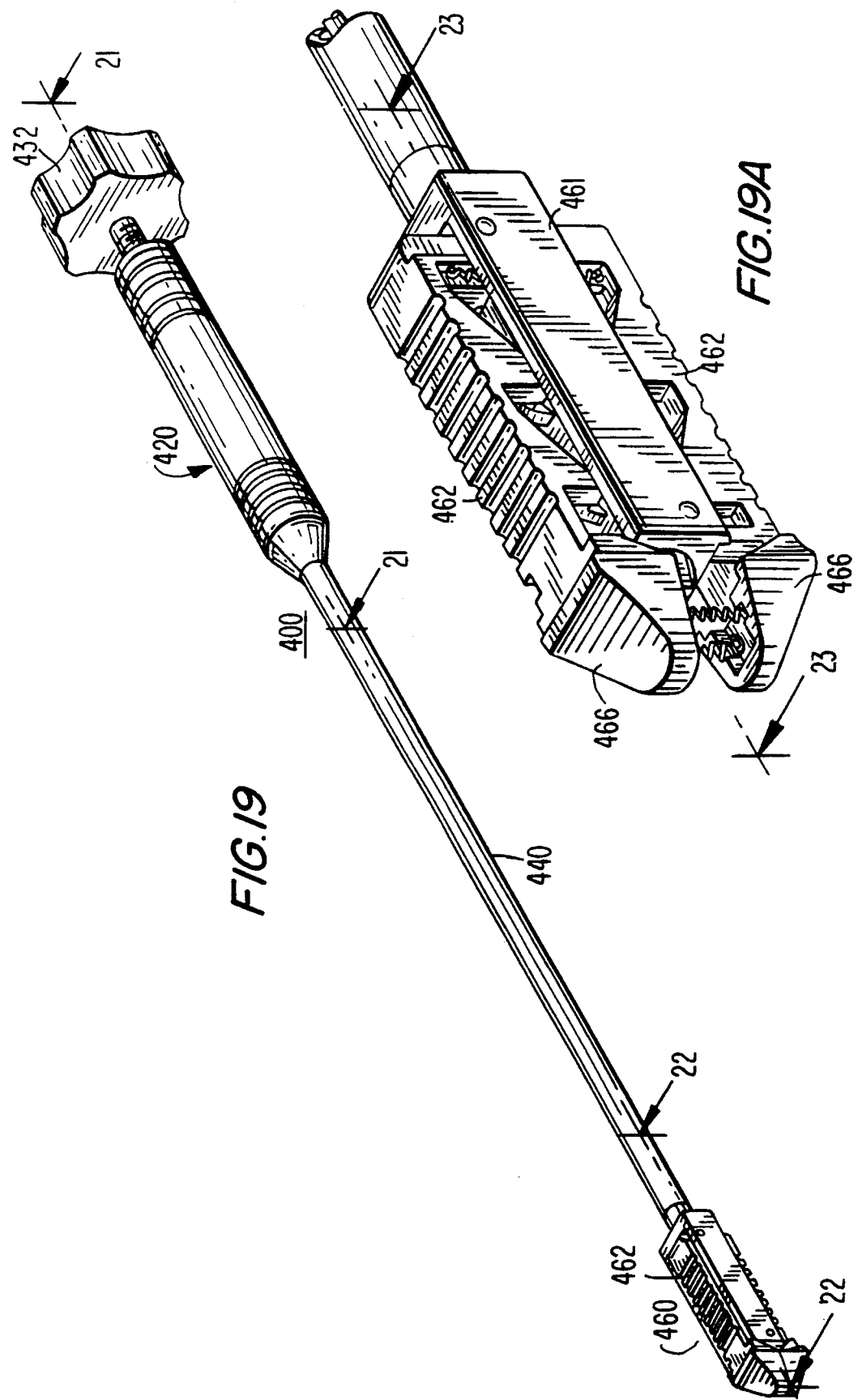

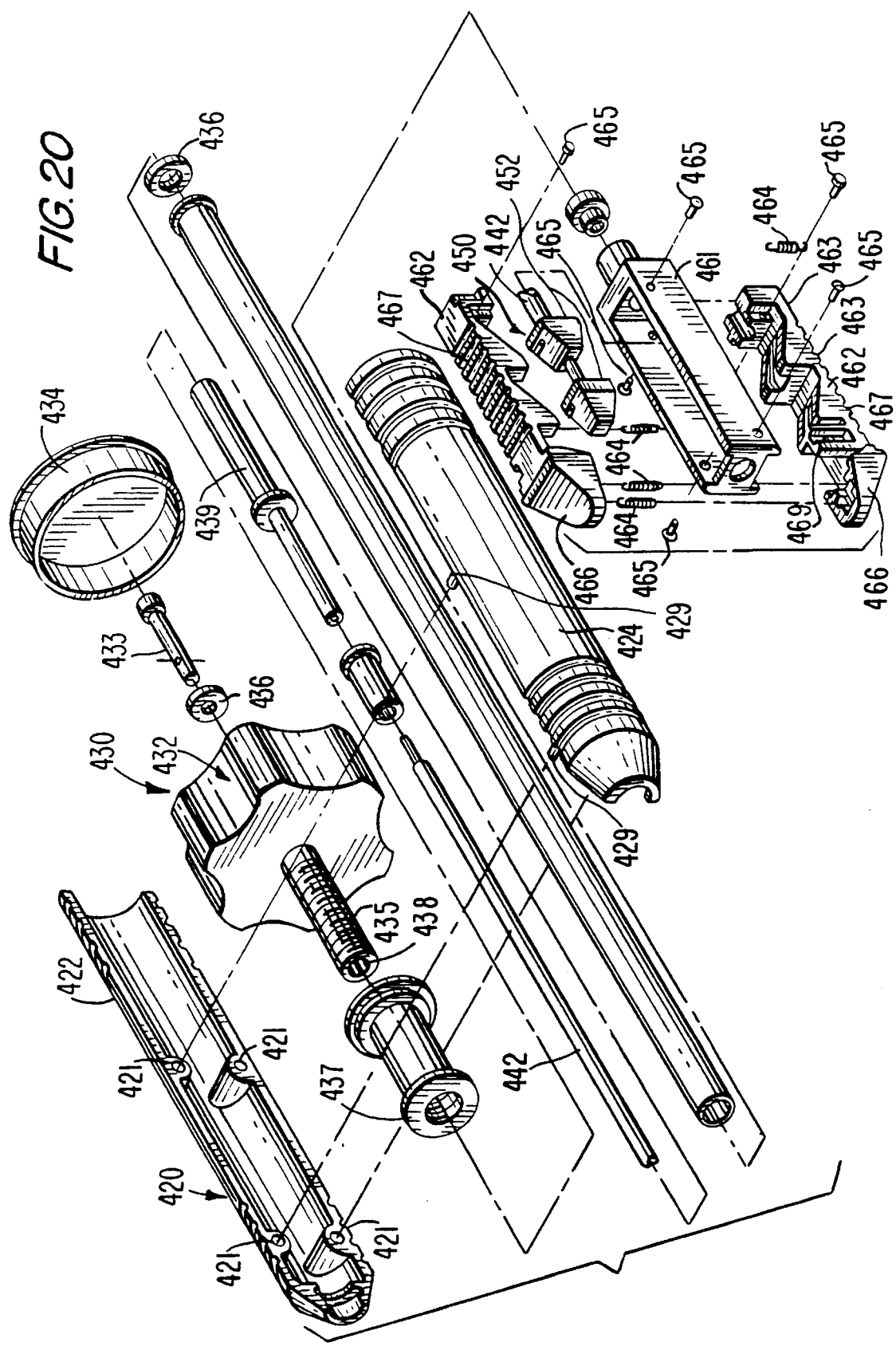

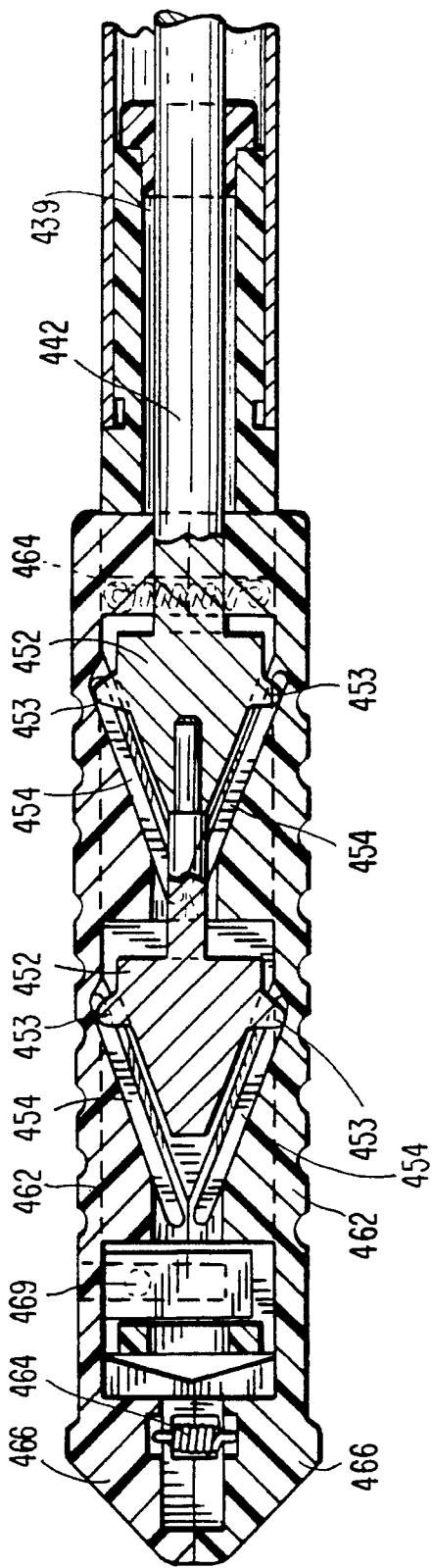

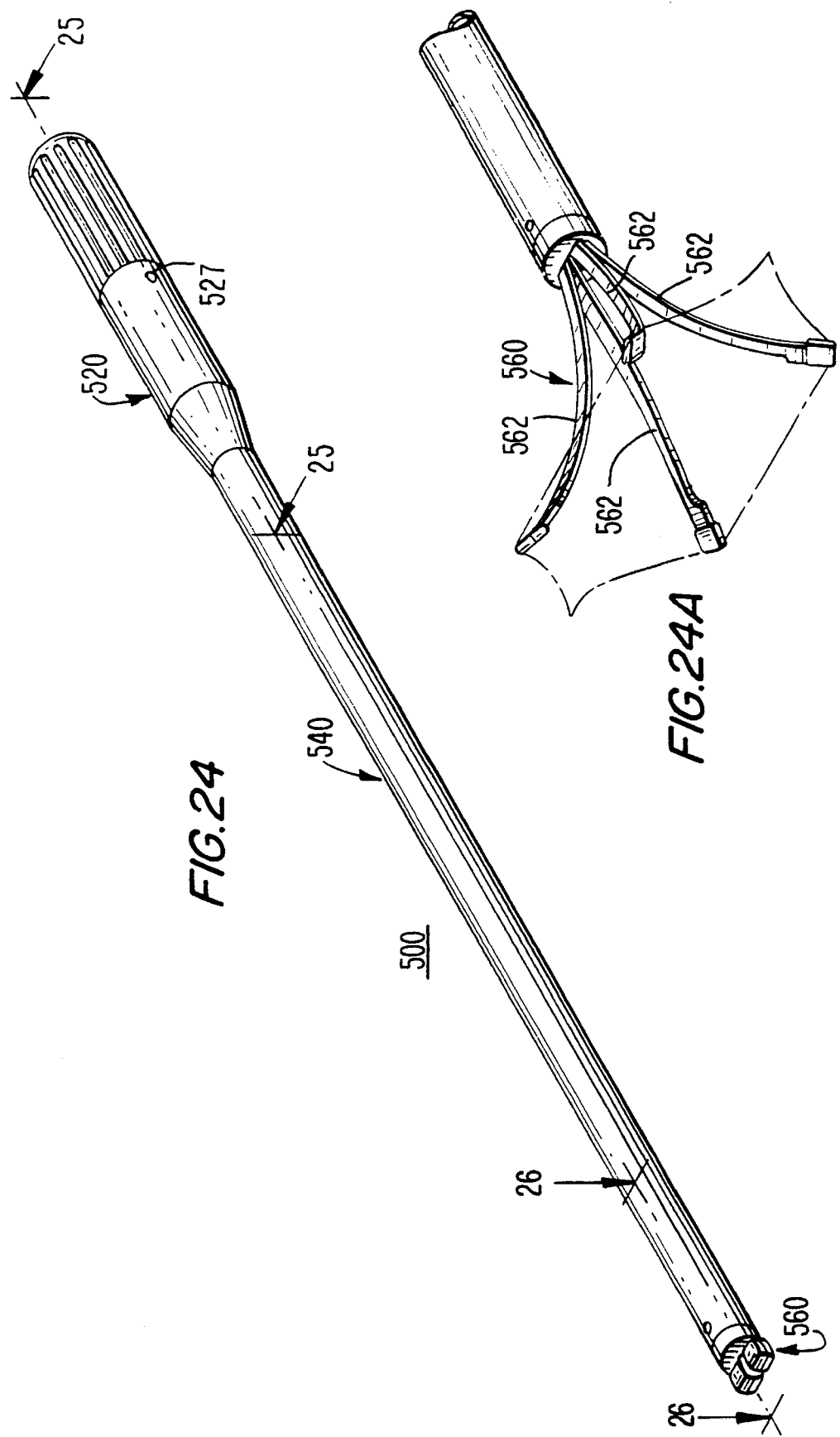

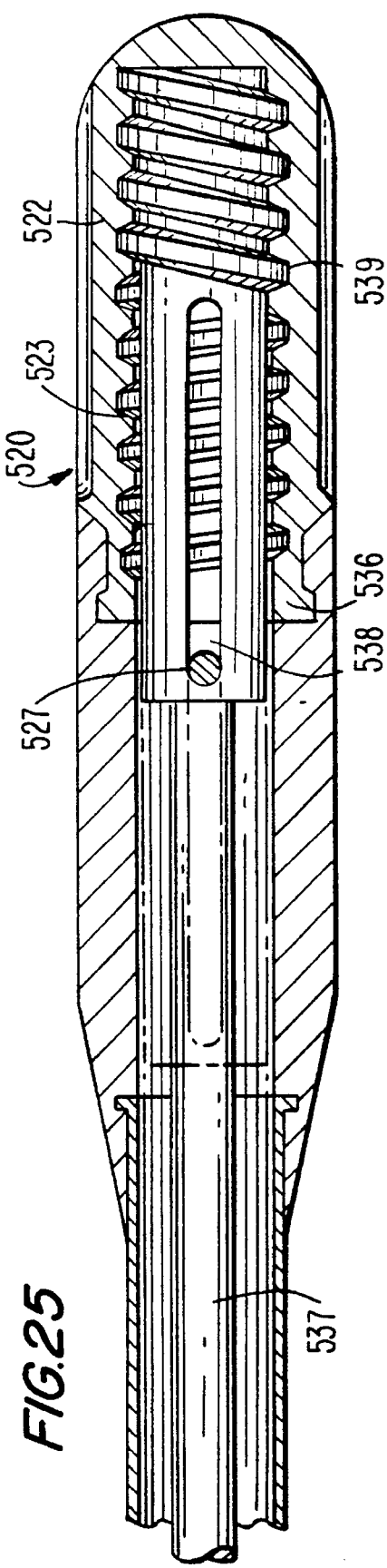
FIG.25
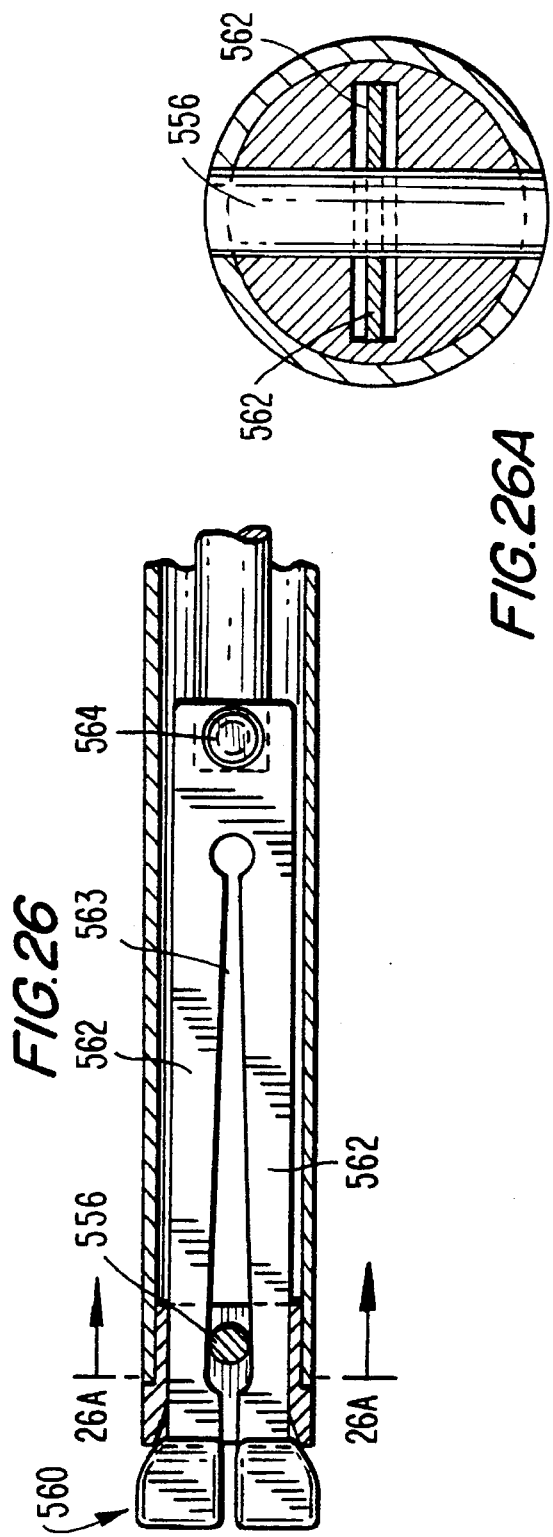
FIG.26A
FIG.26

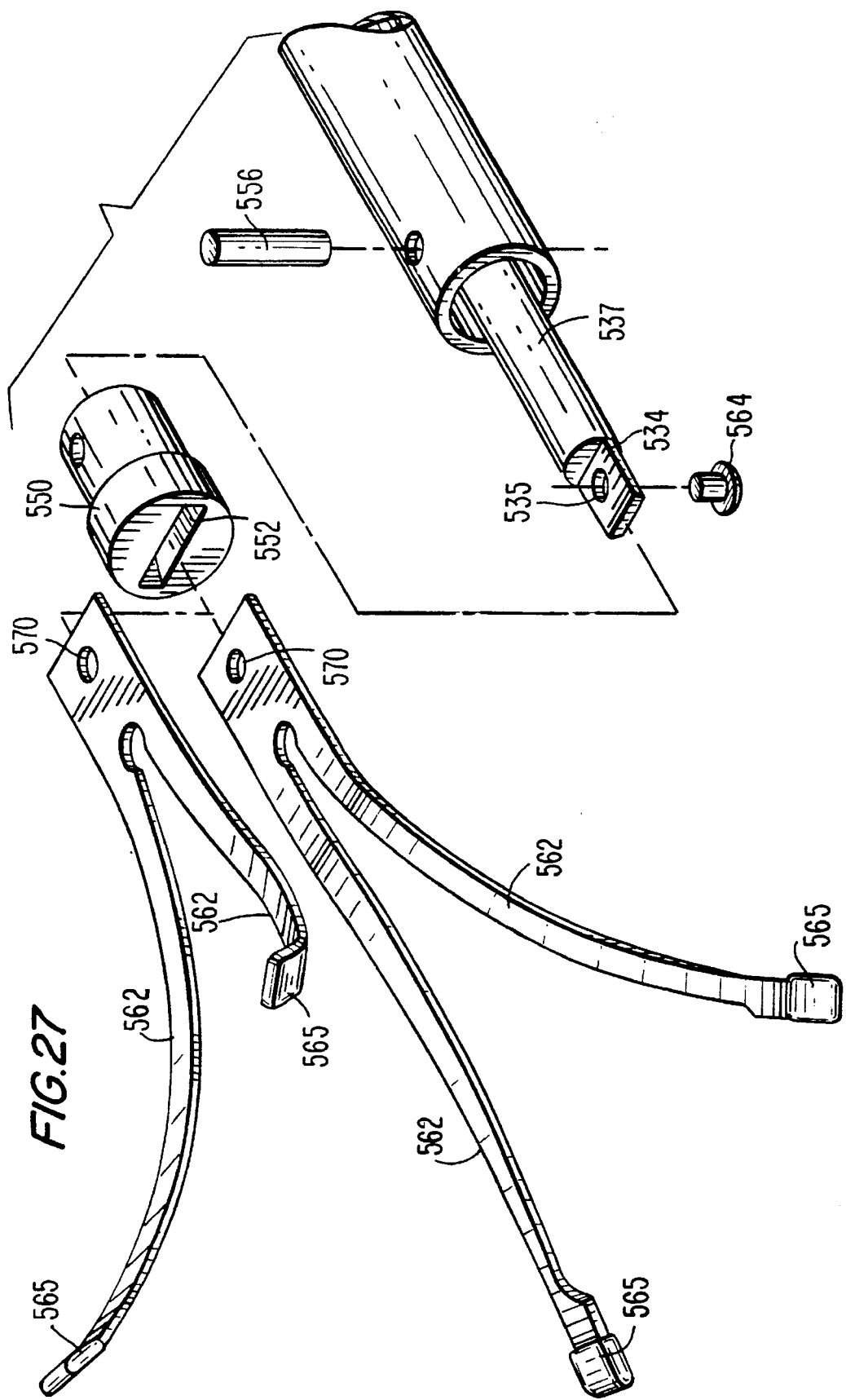

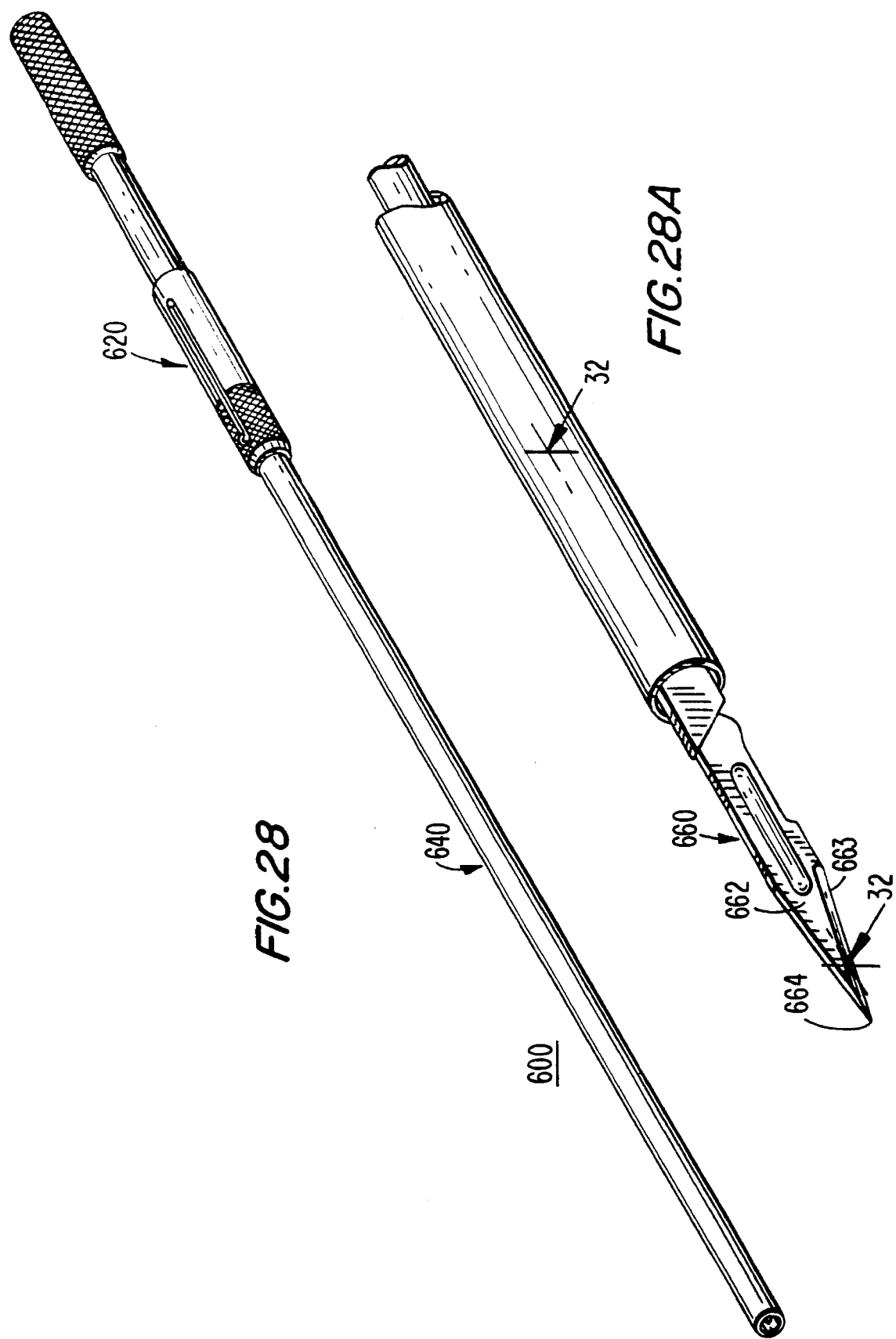

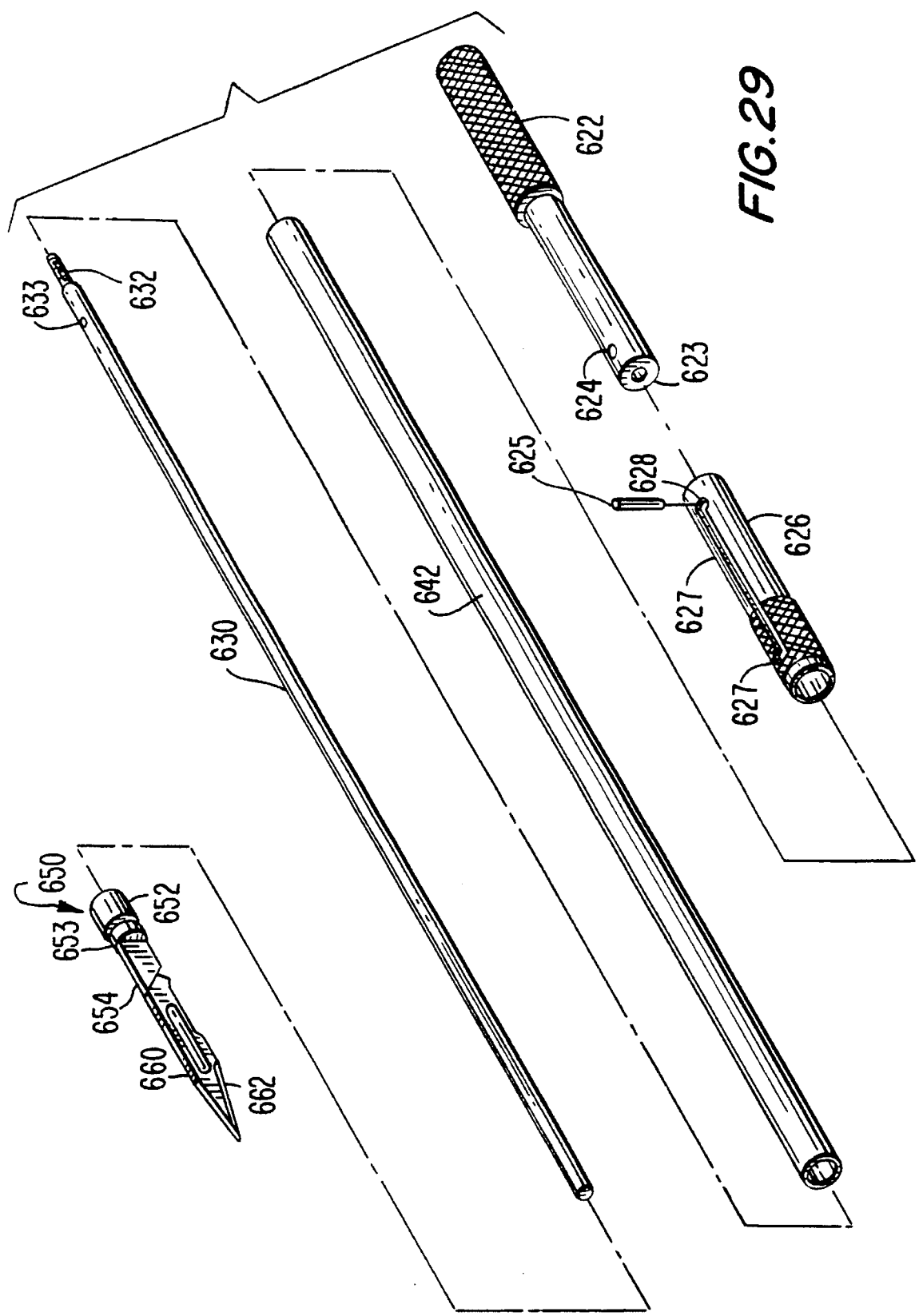

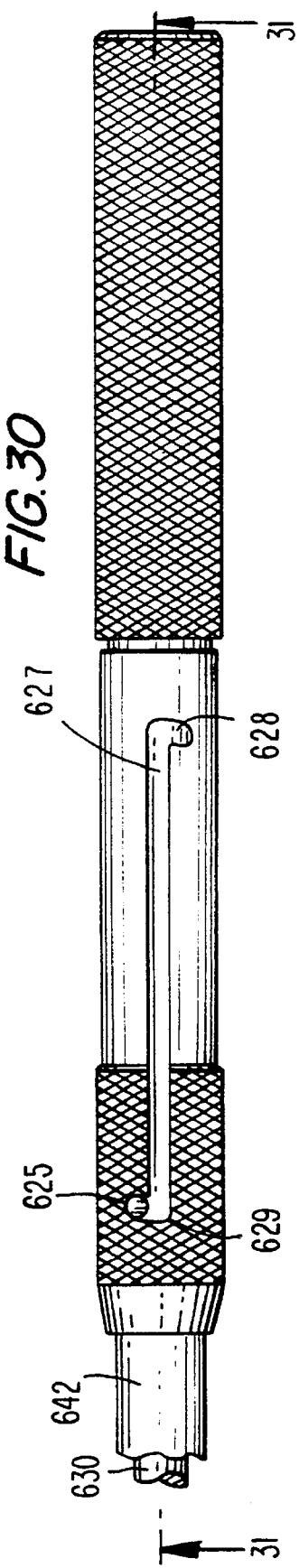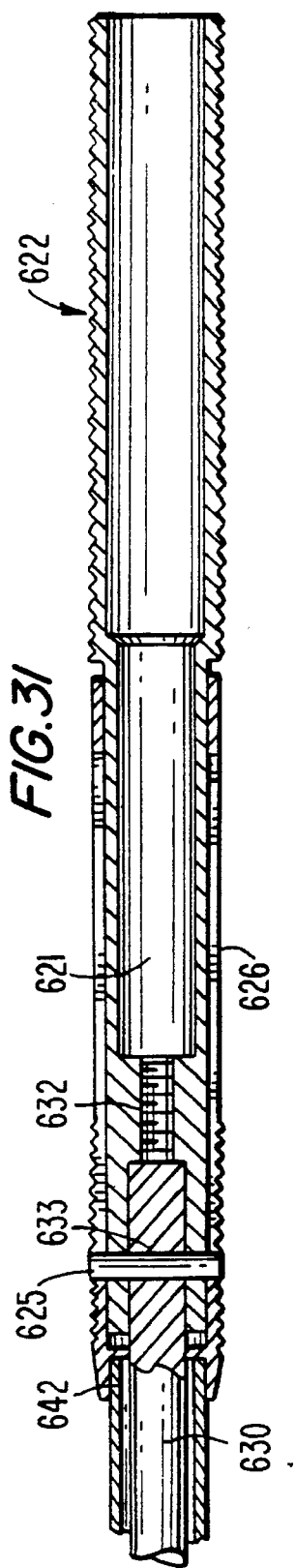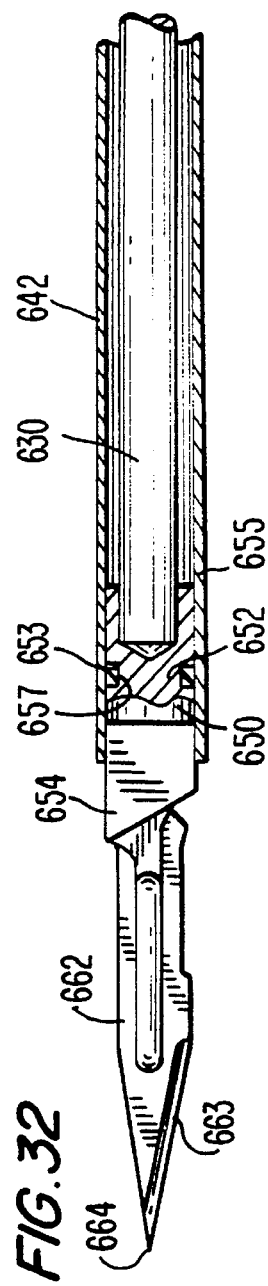

SURGICAL INSTRUMENTS USEFUL FOR ENDOSCOPIC SPINAL PROCEDURES

BACKGROUND OF THE INVENTION

1. Field of the Invention

The invention relates to surgical instruments and, more particularly, to endoscopic surgical instruments useful to perform endoscopic discectomy procedures and other minimally invasive spinal procedures.

2. Description of the Related Art

Back pain is a common affliction affecting millions of people. In many instances, back pain is caused by a herniated intervertebral disc. Intervertebral discs are generally cylindrical-shaped structures corresponding to the margins of the adjacent vertebrae. An outer ring known as the annulus fibrosus composed of concentric layers of fibrous tissue and fibrocartilage surrounds a cartilage-like core known as the nucleus pulposus. When an intervertebral disc is herniated, the softer nucleus projects through a torn portion of the annulus, creating a bulge which extends beyond the intervertebral foramen. As a result of the bulging disc, various spinal nerves may be compressed, causing pain or numbness.

Various procedures are used to treat herniated intervertebral discs. In mild disc herniation, pressure on adjacent nerves is lessened through non-surgical techniques. Such techniques include drugs (analgesics, anti-inflammatory drugs, muscle relaxants), physical therapy, and rest. If these non-surgical approaches are not successful, surgical intervention is necessary. Various surgical procedures have been developed to remove at least a portion of the herniated disc. Such procedures include laminotomies, laminectomies, and percutaneous discectomy.

In laminotomy (also referred to as interlaminar exploration), a posterior approach is used to access the spine through a longitudinal incision. Small amounts of the bony spinal lamina are removed, allowing access to, and removal of, portions of the herniated nucleus pulposus.

Laminectomy is a surgical procedure which, like laminotomy, uses a posterior approach to the herniated disc. In laminectomy, a larger portion of the spinal lamina or laminae are removed to access and remove portions of a herniated disc nucleus. Because both laminotomy and laminectomy require removal of bone and retraction of nerves and muscles, hospitalization and recuperation periods are lengthy. Additionally, removal of bone may lead to future spinal instability.

To minimize the need to remove portions of the vertebrae, other approaches to the herniated disc have been used. In particular, percutaneous discectomy employs a postero-lateral approach. Instruments are inserted through a cannula inserted through the patient's side. The disc annulus is pierced and the herniated nucleus is mechanically disintegrated, the pieces being removed through suction. This technique is shown for example in U.S. Pat. Nos. 4,545,374, 5,242,439 and RE 33,258.

Endoscopic surgery involves incising through body walls via small incisions, generally by use of a trocar having a obturator with a sharp tip removably positioned in a cannula. After penetration, the obturator is removed leaving the cannula positioned in the body for reception of a camera or endoscope to transmit images to a remote TV monitor. Specialized instruments such as forceps, cutters, and applicators are inserted through other trocar sites for performing the surgical procedure while being viewed by the surgeon on the monitor. With the advent of endoscopic surgery and the recognition of its advantages over open procedures in reducing costs by shortening the patient's hospital stay and time of recovery so the patient can resume normal activity sooner, the industry has been viewing endoscopic discectomy as an alternative to the techniques and surgical methods described above. However, to date, the need exists for endoscopic instrumentation to properly and atraumatically improve access to the disc to facilitate removal for successful performance of endoscopic discectomy. The need also exists for improved endoscopic instrumentation to clear a path for removal of the disc as well as to excise the disc.

U.S. Pat. No. 5,195,541 discloses a method for performing lumbar discectomy involving inserting a sleeve having an endoscope receiving means, a laser fiber receiving means and a suction and irrigation channel means. This device, however, is of relatively large diameter because it must accommodate a variety of surgical instruments and therefore may obstruct the surgeon's view (on the TV monitor) and provide limited access to the disc.

There is a need in the art for improved surgical instrumentation which facilitates minimally invasive surgical techniques for anteriorly accessing the herniated disc. The instrumentation and techniques should improve both access to and removal of the disc and permit the surgeon to endoscopically remove any desired amount of disc material with minimal interference to spinal nerves and adjacent back muscles. Such instrumentation and techniques would permit the surgical alleviation of back pain while providing the benefits attendant endoscopic/laparoscopic surgery, namely avoiding large incisions and long periods of hospital stay and patient recovery.

Such instrumentation could also advantageously be used for aiding other minimally invasive surgical spinal procedures such as spinal fusion.

SUMMARY OF THE INVENTION

The present invention provides endoscopic instrumentation and surgical techniques useful for accessing and removing at least a portion of an intervertebral disc. Instrumentation in accordance with the present invention include tissue spreaders and cutting instruments. In particular, the tissue spreading instruments include instruments for spreading pre-sacral tissue such as fascia. Other tissue spreading instruments are especially designed for spreading adjacent vertebrae to facilitate access to the intervertebral disc or for spreading the vertebrae for spinal fusion or other spinal procedures. Endoscopic cutting instruments deliver a cutting blade in a sheathed position to the site of the disc nucleus followed by deployment to remove portions of the disc nucleus.

More particularly an endoscopic surgical instrument for spreading vertebrae is provided which comprises a handle portion including an actuation member, an elongated endoscopic section extending distally from the handle portion and defining a longitudinal axis of the instrument, an actuation mechanism at least partially housed within the endoscopic section and movable in response to movement of the actuation member, and a vertebrae spreading mechanism operatively associated with a distal end portion of said endoscopic section and deployable between closed and open positions by the actuation mechanism in response to movement of the actuation member. The vertebrae spreading mechanism includes first and second vertebrae spreading arm members which are cammed by the actuation mechanism and deployable in a transverse direction with respect to the longitudinal axis of the instrument in response to movement of the actuation member such that said first and second arm members remain substantially parallel to the longitudinal axis of the instrument during deployment.

In an alternate embodiment, a drive chain is positioned between the actuation member and a threaded driving member for rotating the driving member to pivot the vertebrae spreading arm members between the open and closed positions.

The present invention may also provide an endoscopic surgical instrument for cutting tissue which comprises a handle portion including an actuation member and elongated endoscopic portion extending distally from the handle portion. An actuation rod is longitudinally reciprocable within the endoscopic portion and operatively associated with the actuation member. A cutting member is operatively associated with the actuation rod and is movable by the actuation member between a sheathed position within the endoscopic portion and a deployed position in which at least a portion of the cutting member extends distally from the endoscopic portion.

An endoscopic surgical instrument for spreading tissue may also be provided which comprises a handle portion and an elongated endoscopic section extending from the handle portion and having a proximal and distal portion and a longitudinal axis. A resilient tissue spreading mechanism extending from the distal portion of the endoscopic section and the tissue spreading mechanism is removably mounted to the endoscopic section and is spring biased in an open position.

A gaseous sealing member may be disposed within the endoscopic section of these instruments.

BRIEF DESCRIPTION OF THE DRAWINGS

FIG. 1A is a perspective view of the distal end of the instrument of FIG. 1 showing the spreading element in the deployed position.

FIG. 5 is a side cross-sectional view illustrating the handle portion of the instrument of FIG. 1 as the spreading element is deployed.

FIG. 6 is a side cross-sectional view illustrating the distal end of the instrument of FIG. 1 with the spreading element deployed.

FIG. 7 is a perspective view of a first embodiment of an endoscopic surgical instrument for spreading vertebrae according to the present invention.

FIG. 7A is a perspective view of the distal end of FIG. 7 illustrating the vertebrae spreading elements in a deployed position.

FIG. 8 is a side cross-sectional view taken along lines 8—8 of FIG. 7 illustrating the handle portion of the instrument before deployment of the vertebrae spreading elements.

FIG. 9 is a side cross-sectional view taken along lines 9—9 of FIG. 7 illustrating the vertebrae spreading elements in the non-deployed position.

FIG. 10 is a cross-sectional view taken along lines 10—10 of FIG. 9.

FIG. 11 is a side cross-sectional view taken along lines 11—11 of FIG. 7A illustrating the vertebrae spreading elements in the deployed position.

FIG. 12 is a cross-sectional view taken along lines 12—12 of FIG. 11.

FIG. 13 is a perspective view with parts separated of the vertebrae spreading portion of the instrument of FIG. 7.

FIG. 14 is a perspective view of an alternative embodiment of an endoscopic surgical instrument for spreading vertebrae according to the present invention.

FIG. 14A is a perspective view of the distal end of the instrument of FIG. 14 showing the vertebrae spreading arms in an open (deployed) position.

FIG. 17 is a side cross-sectional view of the distal vertebrae spreading portion of the surgical instrument of FIG. 14 with the vertebrae spreading arms in an open (deployed) position.

FIG. 18 is a perspective view with parts separated of the vertebrae spreading portion of the surgical instrument of FIG. 14.

FIG. 19 is a perspective view of another alternate embodiment of an endoscopic surgical instrument for spreading vertebrae according to the present invention.

FIG. 19A is an enlarged perspective view of the distal end of the surgical instrument of FIG. 19 showing the vertebrae spreading elements in a deployed position.

FIG. 20 is a perspective view with the parts separated of the surgical instrument of FIG. 19.

FIG. 22 is a side cross-sectional view taken along lines 22—22 of FIG. 19 showing the vertebrae spreading elements in a closed (non-deployed) position.

FIG. 23 is a side cross-sectional view taken along lines 23—23 of FIG. 19A showing the vertebrae spreading elements of the surgical instrument in a deployed position.

FIG. 24 is a perspective view of an endoscopic surgical instrument for spreading tissue according to another embodiment of the present invention.

FIG. 24A is an enlarged perspective view of the distal end of the endoscopic surgical instrument of FIG. 24 showing the tissue spreading members in an open (deployed) position.

FIG. 25 is a side cross-sectional view taken along lines 25—25 of FIG. 24 illustrating the handle portion of the endoscopic surgical instrument.

FIG. 26 is a side cross-sectional view taken along lines 26—26 of FIG. 24 illustrating the tissue spreading portion of the endoscopic surgical instrument in the non-deployed position.

FIG. 26A is a cross-sectional view taken along lines 26A—26A of FIG. 26.

FIG. 27 is a perspective view with parts separated of the distal end of the endoscopic surgical instrument of FIG. 24.

FIG. 28 is a perspective view of an endoscopic surgical cutting instrument according to the present invention.

FIG. 28A is an enlarged perspective view of the distal end of the endoscopic surgical cutting instrument of FIG. 28 showing the knife blade in an extended position.

FIG. 29 is a perspective view with parts separated of the endoscopic surgical cutting instrument of FIG. 28.

FIG. 30 is an enlarged top plan view of the handle portion of the endoscopic surgical cutting instrument of FIG. 28.

FIG. 31 is a side cross-sectional view of the surgical instrument of FIG. 28 taken along lines 31—31 of FIG. 30.

FIG. 32 is a side cross-sectional view of the distal cutting portion of the endoscopic cutting instrument taken along lines 32—32 of FIG. 28A showing the knife blade in an extended position.

DETAILED DESCRIPTION OF THE PREFERRED EMBODIMENTS

A. Instrumentation

Figure 1:
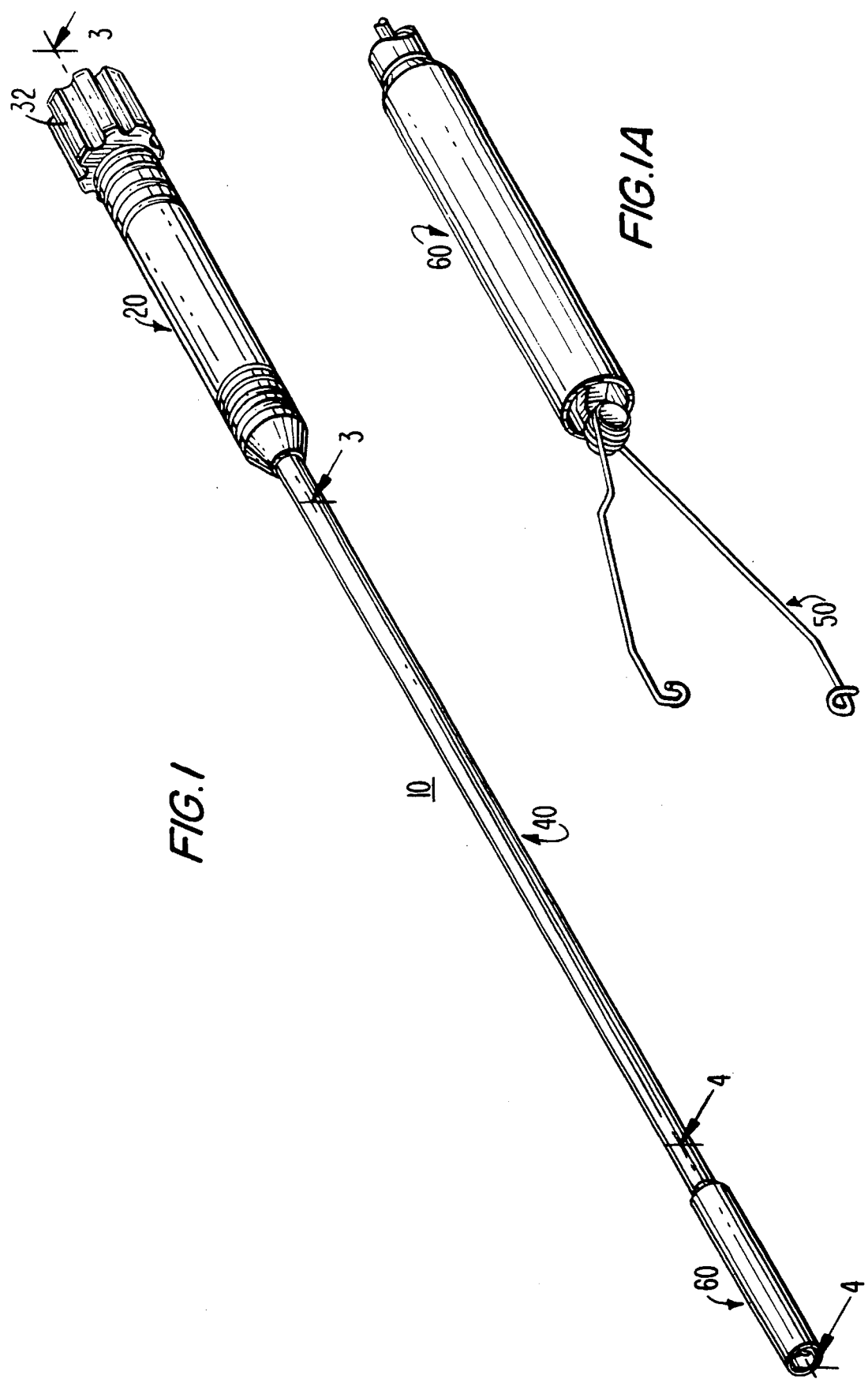
FIG. 1 is a perspective view of an endoscopic surgical instrument for positioning a tissue spreading element according to the present invention.

Turning now to the drawings in detail in which like reference numerals identify similar or identical elements throughout the several views, FIG. 1 depicts an endoscopic surgical instrument 10 which may be used as a tissue spreader and particularly as a fascia spreader during an endoscopic discectomy procedure. In describing the surgical instruments of the present invention, the term "proximal" refers to a direction of the instrument away from the patient and towards the user while the term "distal" refers to a direction of the instrument towards the patient and away from the user.

Surgical instrument 10 includes a handle portion 20 having an actuating member 32 at a proximal end and an elongated endoscopic portion 40 extending from a distal end. Supported at a distal end of endoscopic portion 40 is tissue spreading element housing member 60 which houses tissue spreading element 50, shown in FIG. 1A.

Figure 2:
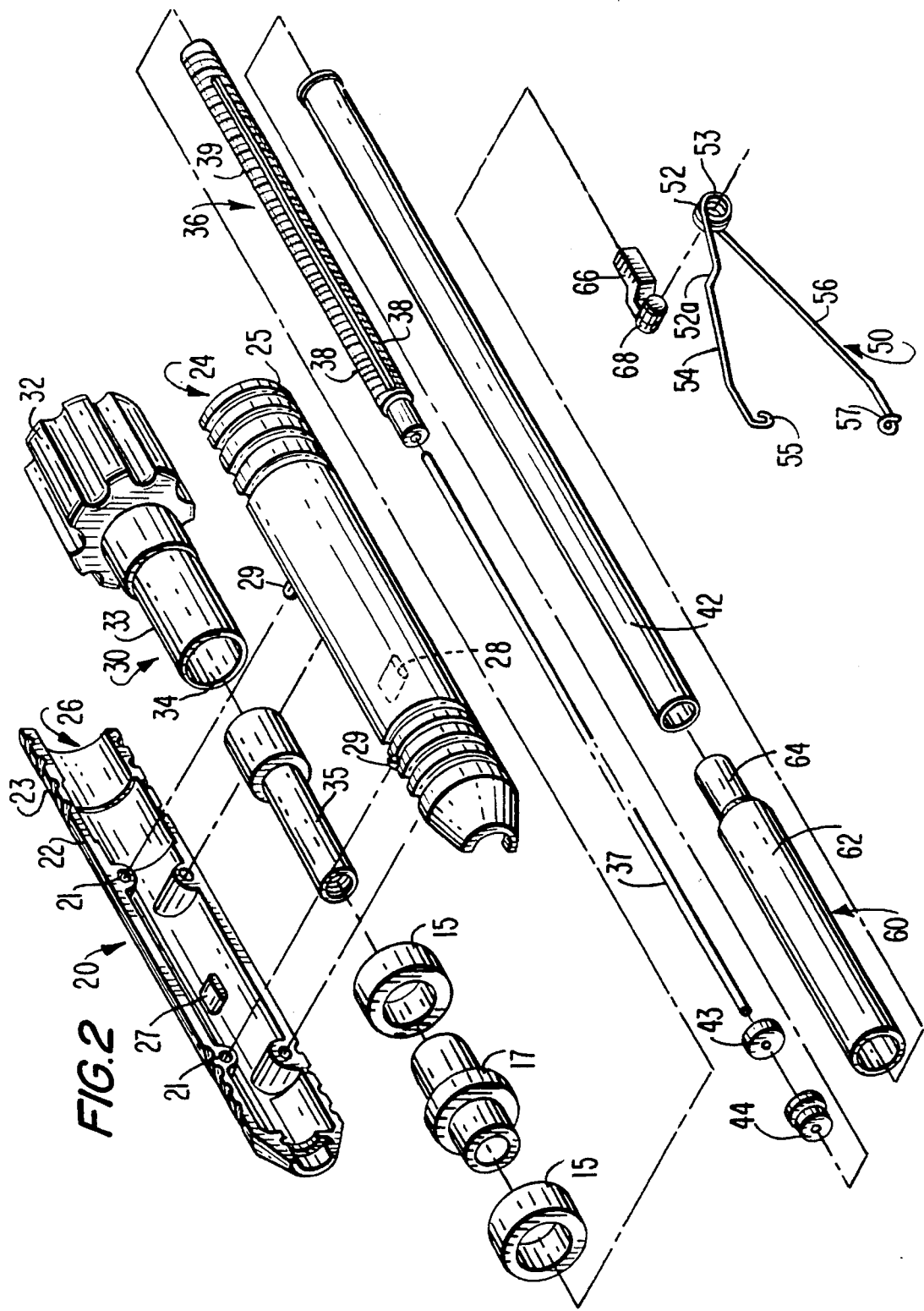
FIG. 2 is a perspective view with parts separated of the surgical instrument of FIG. 1.

As seen in FIG. 2, the handle portion 20 of instrument 10 includes half-sections 22 and 24 having grip-enhancing knurled outer surfaces 23 and 25, respectively. Radially inwardly projecting pins 29 engage corresponding apertures 21 to ensure proper alignment of the handle half-sections 22, 24. When assembled, half sections 22 and 24 define a stepped axial bore 26 which houses the actuation assembly 30.

Figure 3:
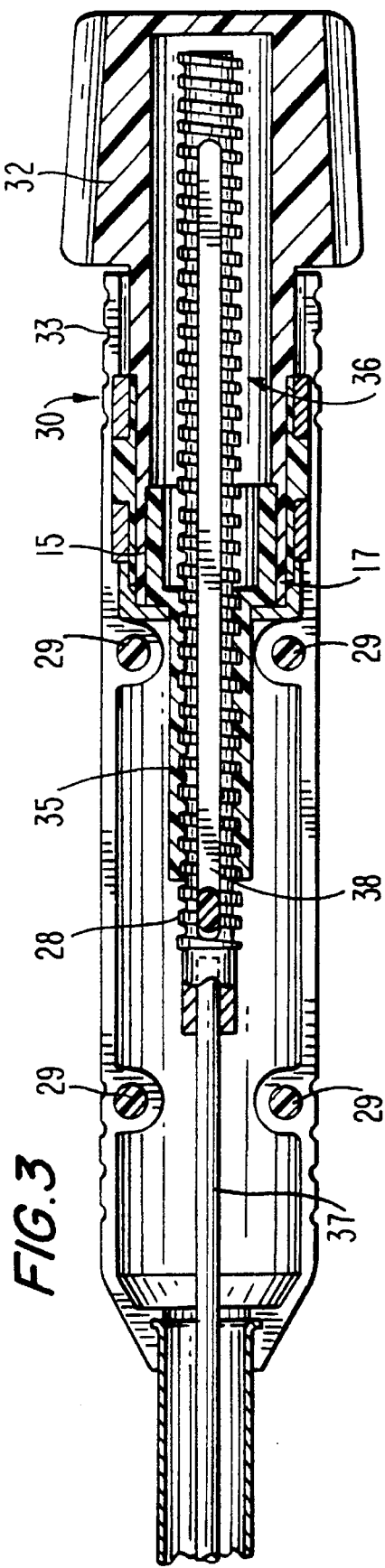
FIG. 3 is a side cross-sectional view taken along lines 3—3 of FIG. 1 illustrating the handle portion of the instrument before deployment of the spreading element.

Referring now to FIGS. 2, 3, and 5, actuation assembly 30 includes a threadably advanceable driving member 36 and an actuating member 32 comprising a rotatable knob having a stepped cylindrical portion 33 extending into axial bore 26 of handle portion 20. Cylindrical portion 33 defines a bore 34 for receiving a stepped cylindrical threaded insert member 35. Rotation of actuating member 32 produces corresponding rotation of insert member 35.

The driving member 36 comprises an elongated threaded body portion 39 which engages threaded insert member 35. At its distal end, driving member 36 includes an axial bore which receives an actuation rod member 37 for positioning tissue spreading element 50. A pair of longitudinal guide slots 38 extend laterally along threaded body 39 of driving member 36. Guide slots 38 cooperatively engage guide pins 27 and 28 which project laterally inward from handle half-sections 22 and 24. The interaction of guide pins 27 and 28 with guide slots 38 permits axial reciprocal motion of driving member 36 and actuation rod 37 while prohibiting rotational motion.

Referring again to FIG. 2, to ensure proper axial alignment of actuation mechanism 30 within the handle and to ensure low friction rotary motion and ability to carry thrust loads, thrust bearing members 15 and bearing sleeve 17 are provided. Thrust bearing member 15 are positioned on both sides of alignment bearing sleeve 17 and the assembly is welded to the distal end of cylindrical portion 33.

The endoscopic portion 40 of surgical instrument 10 includes an elongated, substantially cylindrical member 42. Cylindrical member 42 houses actuation rod 37. A gaseous seal 43 is positioned within cylindrical member 42 to prevent passage of insufflation gas through the surgical instrument. The gaseous seal is provided with a central aperture to permit longitudinal reciprocal motion of actuating rod 37 therethrough. Although gaseous seal 43 is depicted as a gasket-like element which may be fabricated from, e.g., an elastomeric material, it will be appreciated by those skilled in the art that other gaseous seals, e.g., silicone grease, may be used.

A further alignment member or bushing 44 may be provided with the endoscopic portion 40 of the surgical instrument. Alignment member 44 ensures proper positioning and axial movement of the actuating rod 37 within cylindrical member 42.

Figure 4:
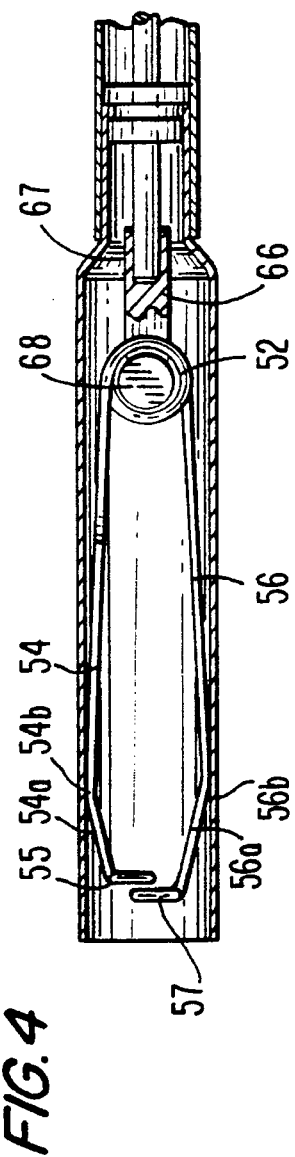
FIG. 4 is a side cross-sectional view taken along lines 4—4 of FIG. 1 illustrating the spreading element within the distal end of the instrument.
Figure 6A:
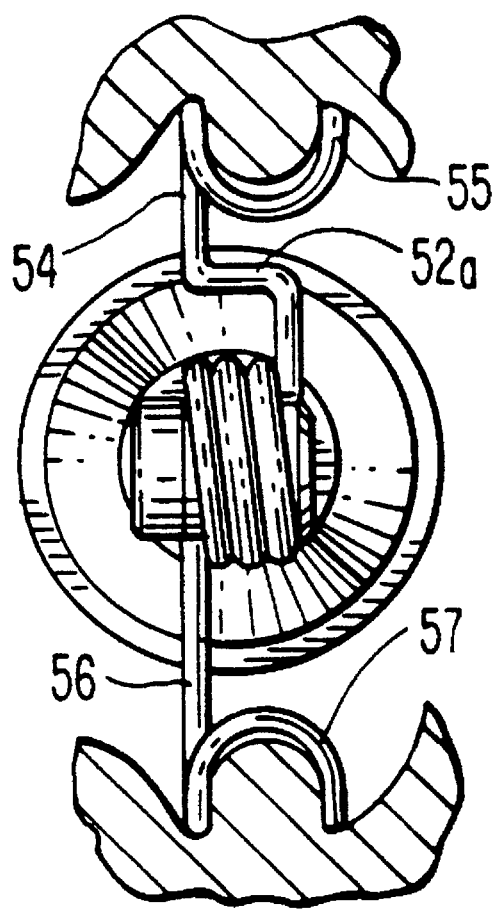
FIG. 6A is a cross-sectional view taken along lines 6A—6A of FIG. 6 illustrating the spreading element spreading tissue.

Referring now to FIGS. 2, 4, and 6, extending from the distal end of cylindrical member 42 is housing 60. Housing 60 includes an elongated cylindrical section 62 which tapers to a narrowed region 64 at its proximal end. Region 64 is configured to provide an interference fit with the distal end of cylindrical member 42 for connecting housing 60 to the endoscopic section of the instrument. Within housing 60, actuating rod 37 terminates in a connector 66. Connector 66 includes bore 67 (FIG. 4) for receiving actuating rod 37 at its proximal end and cylindrical projection 68 at its distal end for removably engaging tissue spreading element 50. Alternatively, rod 37 and connector 66 with projection 68 can be formed as one piece.

Tissue spreading element 50 comprises a torsion spring having resilient tissue spreading arms 54 and 56 extending outwardly from coil portion 52 and terminating in curved hooks 55 and 57. The hooks 55 and 57 curve outwardly away from the respective arms 54 and 56 to facilitate spreading of tissue. Hooks 55 and 57 are offset from one another to prevent entanglement when in the closed position. Tissue spreading elements 54,56 are preferably composed of stainless steel and are biased to a normally open position, as shown in FIGS. 2 and 4. When positioned within housing 60, arms 54 and 56 are compressed radially inwardly as shown in FIG. 4, with hook 55 slightly rearward of hook 57. Arms 54 and 56 are bent radially inwardly in region 54a, 56a to prevent premature opening of the spring as it emerges from the housing. That is, as tissue spreading element 50 initially emerges from housing 60, tissue spreading arms 54 and 56 do not open as regions 54b, 56b are still in abutment with the inner wall of housing 60. When bent portions 54a and 56a (and regions 54b, 56b) are distal of housing 60, tissue spreading arms 54, 56 spread (spring) open to their normally open position. Tissue spreading element 54 also includes a bent portion 52a so that the remaining portions of element 54 lie in the same plane as element 56. This is more clearly shown in FIG. 6a. This symmetrical arrangement provides stability as well as facilitates forming a more uniform opening in the tissue as the tissue portions are spread apart by elements 54, 56.

Coil 52 of the tissue spreading element defines a cylindrical aperture 53 (FIG. 2) configured to releasably receive cylindrical projection 68 of connector 66. When tissue spreading element 50 is deployed, the user can slide connector 66 from within the coil interior and remove surgical instrument 10. Thus, arms 52 and 54 can be left in an open position in the patient's body. At a later time during the surgical procedure, the endoscopic portion can be re-inserted and projection 68 can be inserted into the opening in coil portion 52 to re-engage and retrieve tissue spreading element 50. Actuation member 32 can then be rotated to draw tissue spreading element 50 rearwardly into housing 60 so that arms 54 and 56 are cammed closed by the housing 60, and the entire instrument can be removed.

FIGS. 24–27 illustrates an alternate embodiment a surgical instrument 500 according to the present invention especially useful as a soft tissue spreader and, more particularly, as a fascia spreader. Instrument 500 includes handle portion 520, elongated endoscopic portion 540, and tissue spreading member 560.

As shown in FIG. 25, handle portion 520 includes rotatable portion 522 having threaded interior 523. A driving member 536 includes a threaded body portion 539 which, at its proximal end, engages interior 523. At its distal end, driving member 536 terminates in an actuation rod member 537 coaxially positioned within endoscopic portion 540. Extending laterally along threaded body portion 539 of driving member 536 is a pair of longitudinal guide slots 538 which cooperatively engage guide pin 527 laterally through the handle portion 520, crossing the longitudinal axis of the instrument. The interaction of guide pins 527 with guide slots 538 permits axial reciprocal motion of driving member 536 and actuation rod 537 while prohibiting rotational motion.

Referring to FIGS. 26 and 27, supported at a distal end of actuation rod 537 is tissue spreading member 560. Tissue spreading members 560 comprises two pairs of arms 562 formed by cutting a channel 563 in a sheet of resilient material. In one embodiment, the resilient material can be a shape memory alloy such as Tinel™, available from Raychem Corporation, Menlo Park, Calif. Clearly, other resilient materials can be utilized. The channel 563 in each spreading member 560 progressively decreases in width from the distal to the proximal end to enable the arms to be spread by pin 556 as described below. Each of the four tissue spreading arms 562 terminates in a blunt tip portion 565 configured and dimensioned to atraumatically engage tissue. Tissue spreading members 560 are affixed to the distal end of the actuation rod 537 through fastener 564 passing through apertures 570 and through aperture 535 formed in actuation rod extension 534, best seen in FIGS. 26 and 27.

To maintain axial alignment and ease of axial movement of tissue spreading member 560, insert 550 is provided at the distal end of endoscopic portion 540. Insert 550 is a cap having a narrow longitudinal axial aperture 552 for accommodating the tissue spreading member 560 and is positioned distal of guide pin 556. In use, rotation of handle portion 520 slides actuation rod member 537 and attached tissue spreading element 500 longitudinally. As tissue spreading element 560 slides distally, channel 563 passes over fixed guide pin 556 to spread arms 562 radially outwardly due to the decreasing width of the channel 563. To retract arms 562, handle portion is rotated in the opposite direction to slide arms 562 proximally within endoscopic portion 540. When deployed, the upper arms 562 spread upwardly and outwardly and the lower arms 562 spread downwardly and outwardly, thereby spreading the tissue in these directions to create a large opening. The opening created can be substantially rectangular in configuration as shown for example in FIG. 24a.

FIGS. 7–23 illustrate several embodiments of surgical instruments useful as a tissue spreader and, more particularly, as a vertebrae spreader according to the invention. The vertebrae spreading elements are composed of a substantially rigid material such as stainless steel or rigid polymer. These endoscopic vertebrae can include a gaseous seal such as an O-ring or silicone grease to prevent the egress of gas through the instrument. Referring first to the embodiments of FIGS. 7–13 and more particularly to Figs. 7 and 7A, surgical instrument 100 includes a handle portion 120 having an actuating member 132 at a proximal end and an elongated, substantially cylindrical endoscopic portion 140 extending from a distal end. Surgical instrument 100 terminates in atraumatic tip 144. Proximal to tip 144 is vertebrae spreading mechanism 150. Vertebrae spreading mechanism 150 includes a pair of spreading members 152, shown in a deployed position in FIG. 7A, especially useful for spreading vertebrae during an endoscopic discectomy procedure.

As seen in FIG. 8, actuating member 132 comprises a rotatable knob member provided with a threaded axial interior bore 134. Threaded bore 134 engages a driving member 136 having an elongated threaded body portion 139. At its distal end, driving member 136 connects to driving rod member 137. Lateral longitudinal slots 138 in driving member 136 cooperate with through-pin 128 to permit axial translation of driving member 136 while prohibiting rotational movement.

Referring now to FIGS. 7 and 13, endoscopic section 140 includes a substantially cylindrical member 142 having slots 146 formed in a distal end thereof to accommodate the tissue spreading mechanism 150. Driving rod 137 coaxially traverses cylindrical member 142 to actuate the tissue spreading mechanism.

Vertebrae spreading mechanism 150 includes a pair of radially deployable serrated vertebrae spreading elements 152 linked together and biased to a non-deployed (closed) position through coil springs 160. Coil springs 160 are mounted by fasteners 162 within recesses 154 formed in the exterior of vertebrae spreading elements 152, best seen in FIGS. 10, 12, and 13.

As shown in FIG. 13, positioned at a distal end of driving rod 137 are a pair of camming elements 135 which deploy vertebrae spreading elements 152 through interaction with camming surfaces located on the inner surfaces 156 of the vertebrae spreading elements 152. Each camming element 135 includes a distal cylindrical portion 131 and a proximal frustoconical portion 133 tapering distally from the cylindrical portion.

When the vertebrae spreading elements 152 are in the retracted position, inner camming surfaces 156 create a stepped axial bore (see FIGS. 9, 11, and 13) defining a proximal frustoconical-shaped portion 157 adapted to engage proximal camming element 135 and tapering to a cylindrical bore 158 of diameter sufficient to accommodate driving rod 137. The diameter of cylindrical bore 158 stepwise increases (in distal direction) in region 159 to accommodate cylindrical portion 131 of distal camming element 135. From region 159, the bore tapers distally to define a frustoconical-shaped distal surface 155 which accommodates frustoconical portion 133 of distal camming element 135.

Atraumatic tip 144 is provided with a stepped axial bore 143 having a proximal frustoconical portion 147 and a cylindrical distal portion 148, best seen in FIG. 9. Stepped bore 143 provides a distal terminus for driving rod 137 and distal camming element 135 when vertebrae spreading elements 152 are in their deployed positions.

In use, rotation of actuating member 132 produces axial translation of driving member 136 and driving rod 137. Proximal camming element 135 moves distally through endoscopic member 142 as distal camming element 135 traverses cylindrical bore portion 159. During this initial motion, vertebrae spreading elements 152 remain stationary in their undeployed position as shown in FIG. 9. Vertebrae spreading elements 152 maintain the position shown in FIG. 9 until frustoconical portion 133 of proximal camming element 135 is positioned within proximal frustoconical bore portion 157 of vertebrae spreading elements 152 and frustoconical portion 133 of distal camming element 135 is positioned within distal frustoconical bore portion 155 of vertebrae spreading elements 152.

As frustoconical portion 133 of distal camming element 135 slides against distal frustoconical bore surface 155 and frustoconical portion 133 of proximal camming element 135 slides against proximal frustoconical bore surface 157, vertebrae spreading elements 152 are biased radially outwardly against the force of connector springs 160, as shown in FIGS. 11 and 12. The vertebrae spreading elements 152 continue moving radially outwardly until the are fully deployed. Full deployment corresponds to the position shown in FIG. 11 with the frustoconical portion 133 of distal camming element 135 fully engaged within frustoconical bore of elements 152. Thus, parallel movement, i.e. movement of vertebrae spreading elements in a direction transverse to the longitudinal axis of the instrument so the elements remain in planes substantially parallel to the longitudinal axis, is achieved. Rotation of actuating member 132 in the opposite direction retracts driving rod 137 and the vertebrae spreading elements 152 return to the original retracted position under the force of springs 160.

Figure 15:
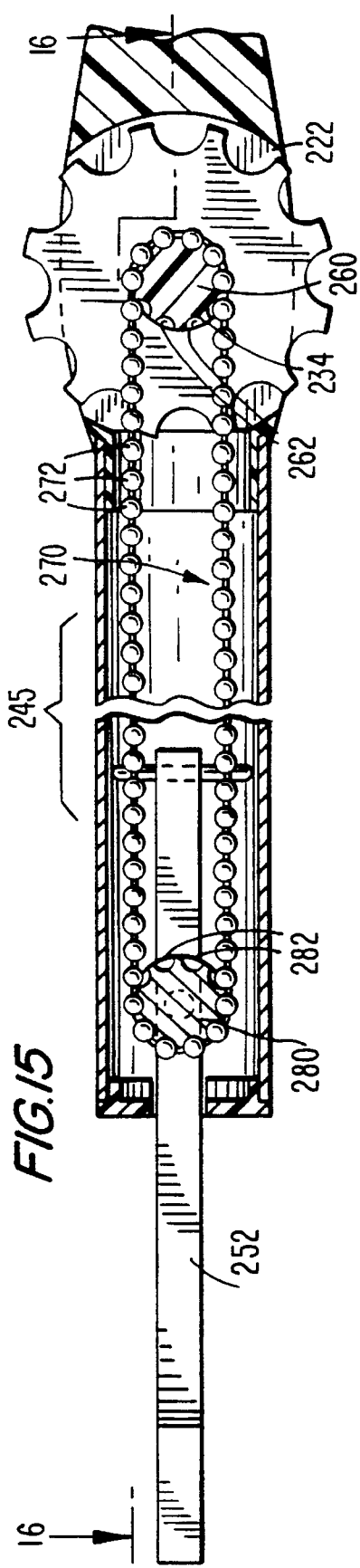
FIG. 15 is a side cross-sectional view of the surgical instrument taken along lines 15—15 of FIG. 14 with the vertebrae spreading arms in the non-deployed position.
Figure 16:
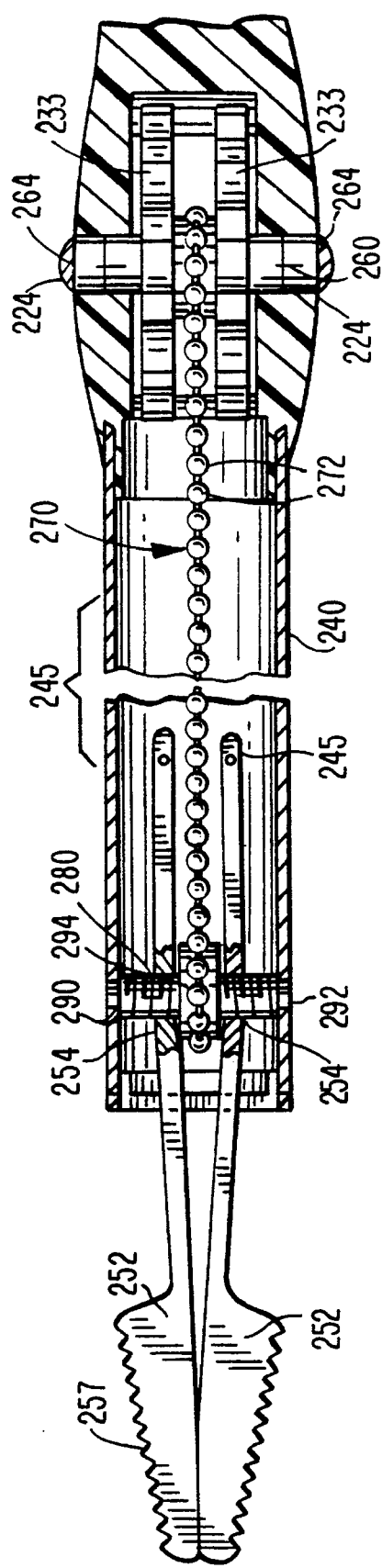
FIG. 16 is a top plan cross-sectional view of the surgical instrument taken along lines 16—16 of FIG. 15 showing the vertebrae spreading arms in the non-deployed position.
Figure 21:
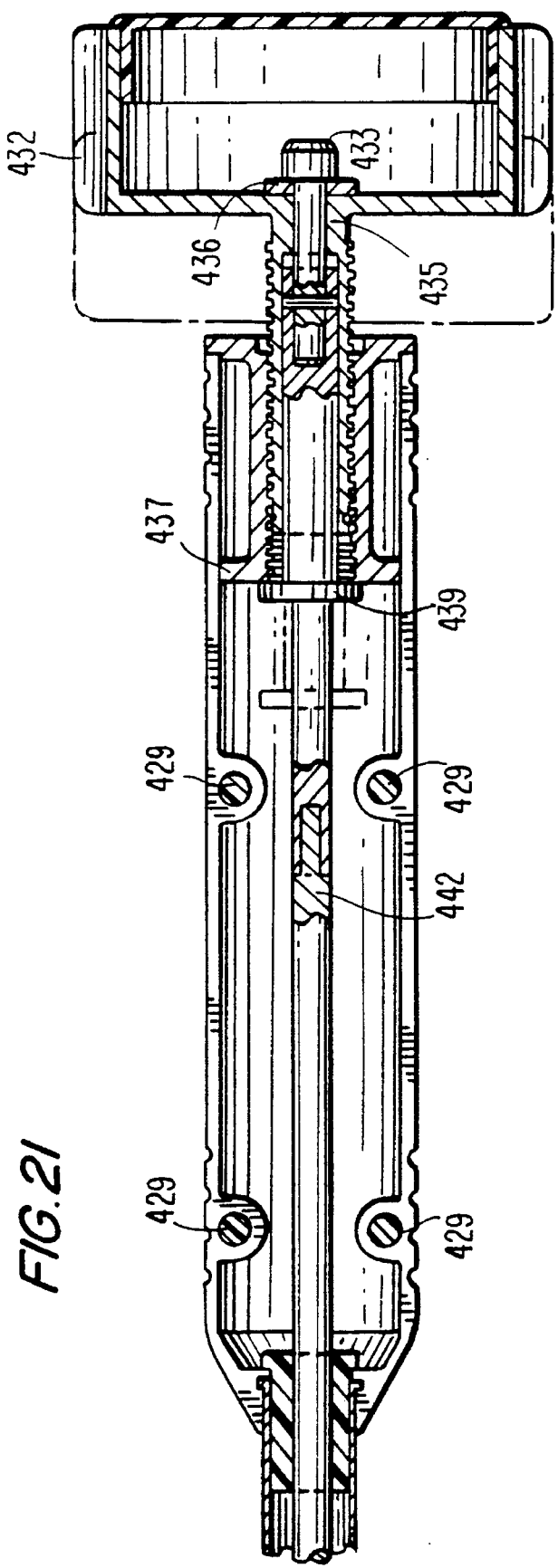
FIG. 21 is a side cross-sectional view taken along lines 21—21 of FIG. 19 showing the handle portion of the surgical instrument.

FIGS. 14–18 depict an alternative embodiment of a surgical instrument 200 useful as a tissue spreader and, more particularly, as a vertebrae spreader, according to the present invention. Vertebrae spreader 200 comprises a handle portion 220 housing an actuating member 232 and an elongated, substantially cylindrical endoscopic portion 240 extending from a distal end of the handle portion. A vertebrae spreading mechanism 250 is coupled to a distal end of the endoscopic portion. Vertebrae spreading mechanism 250 includes radially pivotal vertebrae spreading arms 252 mounted to endoscopic portion 240 through fasteners 245. Vertebrae spreading arms 252 extend through the distal end cap 247 of endoscopic portion 240. As best seen in FIG. 16, the vertebrae gripping surface 257 of each of vertebrae spreading arms 252 forms an acute angle of elevation, angle T, with the longitudinal axis towards the proximal end of instrument 200. This configuration aids in spreading vertebrae since the distalmost portion of the vertebrae spreading arms are narrower than the proximalmost portion, enabling insertion of the instrument within confined spaces.

As illustrated in FIGS. 15 and 16, handle portion 220 includes a chamber 222 for housing actuating member 232 and a through-bore 224 to engage portions of the driving mechanism. Actuating member 232 comprises a pair of rotatable toothed wheels 233 having central circular apertures 234 formed therein. Apertures 234 engage a drive sprocket 260 in an interference fit such that drive sprocket 260 rotates concurrently with wheels 233. Drive sprocket 260 traverses the width of handle portion 220, extending through handle bore 224 where it is fixed at each end by pivotal end caps 264.

Drive sprocket 260 engages a drive chain 270 through a circumferential array of hemispherical grooves 262 spaced to grip and drive adjacent spherical links 272 of drive chain 270. Drive chain 270 extends through endoscopic portion 240 of instrument 200 to a drive sprocket 280. Like drive sprocket 260, sprocket 280 includes a circumferential array of hemispherical grooves 282 which are engaged by spherical links 272 of drive chain 270.

Sprocket 280 circumscribes transverse threaded rod 290 for pivoting vertebrae spreading arms 252. Fasteners 245 are mounted through apertures 256 as pivot points, and vertebrae spreading arms 252 are spread radially outward by threaded rod 290 interengaging their threaded apertures 254. Threaded rod 290 is divided into right and left threaded half sections 292 and 294 respectively. As threaded rod 290 rotates, both arms 252 are pivoted radially outward through provision of rod half sections threaded in opposite directions.

In use, counterclockwise rotation of actuating member 232 produces a corresponding rotation of drive sprocket 260. Drive sprocket 260 drives chain 270 counterclockwise, resulting in counterclockwise rotation of sprocket 280 and threaded rod 290. Engagement of right and left threaded portions 292 and 294 of rod 290 with threaded apertures 254 of vertebrae spreading arms 252 pivots the arms 252 radially outward about pivot points 245, as shown in FIG. 17.

FIGS. 19–23 illustrate another alternative embodiment of a surgical instrument 400 useful as a tissue spreader, and, more particularly as a vertebrae spreader according to the present invention. Surgical instrument 400 comprises handle portion 420 having an actuating member 432 extending proximally therefrom. Elongated, substantially cylindrical endoscopic portion 440 extends distally from the handle portion 420. A vertebrae spreading mechanism 460 is coupled to a distal end of endoscopic portion 440. Vertebrae spreading mechanism 460 includes a housing 461 mounting a pair of vertebrae spreading arm members 462, shown in an open position in FIG. 19A.

As shown in FIG. 20, the handle portion 420 includes handle half-sections 422 and 424 having grip-enhancing knurled outer surfaces. Radially inwardly projecting pins 429 engage corresponding apertures 421 to ensure proper alignment of the half-sections 422, 424. When assembled, half sections 422 and 424 define an axial bore 426 which houses the actuation assembly 430.

Actuation assembly 430 includes a rotatable knob member 432 capped with an end cap 434 and having an externally threaded proximally-extending cylindrical portion 435 defining an interior bore 438. The cylindrical portion 435 is threadably engaged within internally threaded spool-shaped retainer 437 which interfits within the axial bore 426 of the handle portion 420 of the instrument. Retainer 437 maintains the axial alignment of rotatable knob member 432 and provides a distal end point for the knob member 432.

Received within interior bore 438 of knob member 432 is actuating link 439 having an internally threaded bore. Bolt 433 fixes actuating link 439 within bore 438. Longitudinally extending bolt 433 extends through a washer 436 into the cylindrical portion 435 of knob member 432 where it is threadably engaged within the actuating link 439. The relationship of bolt 433 within the knob 432 is such that the bolt does not rotate as the knob is turned, but translates distally along the longitudinal axis with the knob. Consequently, actuating link 439 is translated distally, without any rotational motion component.

Referring now to FIGS. 20, 22 and 23, actuating link 439 fixedly receives an actuating rod 442 within its distal bore. Actuating rod 442 coaxially extends through the endoscopic portion 440 of the instrument and terminates in a camming mechanism 450. Camming mechanism 450 includes a pair of wedge-shaped camming elements 452 for engaging camming surfaces 463 of vertebrae spreading arm members 462. Camming elements 452 include projections 453 to interfit with grooves 454 in the camming surfaces 463 of the vertebrae spreading arms 462. The system of grooves 454 and projections 453 ensure axial alignment of the vertebrae spreading arms 462 as they are deployed and serve as a return mechanism for the arms.

Vertebrae spreading arms 462 are connected to housing 461 and biased to a closed position by four tension coil springs 464. Each spring 464 is fastened at a first hook-shaped end to housing 461 and fastened at the opposite hook-shaped end to vertebrae spreading arm 462 through fasteners 465. To ensure axial alignment of the arms 462, groove and alignment pin system 469 is provided on the interior portion. When mounted to housing 461 in the closed position, FIGS. 19 and 22, knurled exterior portion 467 of arm 462 is flush with the edges of housing 462, while camming surfaces 463 are seated over camming elements 452 within the housing interior.

Distal wedge-shaped nose portions 466 of the vertebrae spreading arm 462 extend beyond the distal end of housing 461 to initially engage the tissue structure to be spread. This allows the instrument 400 to be placed within confined spaces, such as between vertebrae bodies, and gradually spread apart adjacent members.

When surgical instrument 400 is actuated through rotation of knob 432, the camming elements 452 of actuating rod 442 are driven distally, forcing the vertebrae spreading arms 462 radially outward against springs 464 as shown in FIG. 23. Rotation of knob 432 in the opposite direction pulls actuating rod 442 and its associated camming elements 452 in the opposite direction, allowing the vertebrae spreading arms 462 to return to their original retracted position under the force of coil springs 464.

Figure 23A:
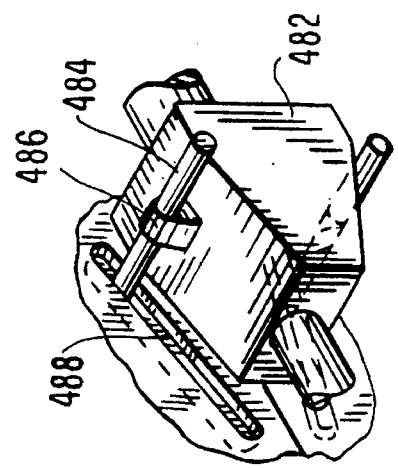
FIG. 23A is a perspective view of an alternate structure for retaining the vertebrae spreading elements of FIG. 22.

In an alternate embodiment shown in FIG. 23A, which eliminates springs 464, camming elements 482 (only one is shown) of camming mechanism 450 includes a transverse guide pin 484 mounted via support 486 and extending into a elongated slot 488 formed in each of the vertebrae spreading arms. The slot 488 is dimensioned to loosely receive guide pin 486 so that during the movement of the arms to the open position, the guide pin 488 does not bear any load. However, during return of the arms to their closed position, the pin 488 rides in the bottom edge of slot 488 and partially bears the load.

FIGS. 28–32 illustrate a shielded endoscopic cutting implement 600 according to the present invention. Endoscopic cutting implement 600 is especially useful for cutting a herniated nucleus pulposus during an endoscopic discectomy procedure, although it can be used in other procedures. Endoscopic cutting implement 600 includes a handle portion 620, an elongated endoscopic portion 640, and a distal knife portion 660, shown in the deployed position in FIG. 28A.

As best seen in FIGS. 29–31, handle portion 620 comprises a stepped cylindrical actuation member 622 having an axial bore 623 with a longitudinally extending threaded fastener 632 received therein. Distal portion 621 of cylindrical actuation member 622 is received within a sleeve member 626 such that it is rotatable and axially translatable within the sleeve member. Sleeve member 626 includes a longitudinal slot 627 for engaging an actuation pin 625. The longitudinal slot 627 has transversely extending notch portions 628 and 629 respectively formed in its proximal and distal ends for engaging an actuation pin 625 in the closed and open positions of the instrument. Aperture 624, formed within narrowed distal portion 621 of actuation member 622, receives actuation pin 625.

Endoscopic section 640 includes an endoscopic tubular member 642 secured within the distal end of sleeve 626 and extending distally therefrom. The endoscopic section 640 further includes an actuation rod 630 having a threaded axial shaft at its proximal end. Actuation rod 630 coaxially extends through the endoscopic tubular member 642 and sleeve 626 to threadably engage threaded bore 632 of actuation member 622. Actuation rod 630 is provided with transverse bore 633 adjacent its proximal end for receiving actuation pin 625.

At its distal end, actuation rod 630 terminates in knife blade housing 650. As seen best seen in FIG. 32, blade housing 650 has a cylindrical proximal portion 652 having a bore 655 for receiving the distal end of actuation rod 630. Proximal portion 652 of housing 650 further includes a circumferential groove 657 to seat gaseous seal member 653. Although illustratively depicted as an O-ring, the gaseous seal may comprise silicone grease or other known gaseous seals.

At its distal end, blade housing 650 terminates in a narrow slit 654 which forms an oblique angle with respect to the longitudinal axis of the instrument. Housing slit 654 frictionally engages a knife blade 662. Knife blade 662 has cutting edge 663 and tapers distally to form pointed tip 664. It is understood by those skilled in the art that variously configured knife blades may be received within housing member 650 depending upon the type of surgical procedure to be performed.

In use, surgical instrument 600 is provided with the knife blade 662 retracted within endoscopic tubular member 642. This position corresponds to actuation pin 625 located within proximal notch 628 of longitudinal slot 627 of sleeve member 626. To extend knife blade 660, cylindrical actuation member 622 of handle portion 620 is rotated clockwise (as viewed from the proximal to distal end) to move actuation pin 625 into the longitudinal portion of slot 627. Actuation member 622 is then advanced distally within sleeve 626 and actuation pin 625 travels distally within slot 627. As actuation member 622 moves distally, actuation rod 630 extends housing 650 and knife blade 662 beyond the endoscopic tubular member 642. When actuation pin 625 reaches the distal end of longitudinal slot 627, the knife blade 662 is fully extended. To lock the knife blade 660 in its extended position, the handle portion cylindrical member 622 is first rotated clockwise to move actuation pin 625 into distal notch 629. To retract knife blade 660, actuation member 622 is rotated in the opposite direction so that actuation pin 625 is moved into the longitudinal portion of slot 627 and then pulled proximally. Rotation of pin 625 into proximal notch 628 will lock the knife blade 660 in the retracted position.

B. Surgical Method

Use of the surgical instruments of FIGS. 1–32 will be described in conjunction with an anterior endoscopic lumbar discectomy according to the present invention. While they have particular application in this procedure, it is recognized that the instruments of the present invention may be used to perform surgical spreading and cutting procedures anywhere in the body. In describing the procedure, the term "anterior" is broadly used to describe the ventral surface of a body opposite the back. This term includes, but is not limited to, the abdominal region of the body.

For performing an anterior endoscopic lumbar discectomy, the patient is placed in the supine position and entry is made through the abdomen, which is insufflated according to known procedures. Specific points of entry are determined by the particular intervertebral disc to be removed. For removal of intervertebral discs of the lumbar vertebrae, ports are established in the lower abdomen using standard trocars. One port is dedicated to viewing via an endoscope, while remaining ports are used for surgical instrument insertion and manipulation.

To access the intervertebral disc, soft tissue is dissected, providing a pathway through the abdominal region. Fascia and other soft tissue may be spread using the tissue spreader of FIG. 1 or FIG. 24. Organs such as the colon are retracted away from the operating site to increase exposure and facilitate observation of the spinal column.

Upon reaching the spinal column, blunt dissection is performed to expose the intervertebral disc. Fascia is removed from the disc area and spread using the tissue spreader of FIG. 24 to create an access opening or by placing a tissue spreading element in the fascia using the instrument of FIG. 1.

To further facilitate access to the intervertebral disc, the adjacent vertebrae are spread using any of the vertebrae spreaders of the present invention. The distal end of the selected instrument is placed between the vertebral bodies. Deployment of the vertebrae spreader causes the arms to expand against each adjacent vertebral body, relieving pressure on the disc to ease disc removal.

The herniated disc nucleus is accessed through the disc annulus. The disc annulus may be incised using the endoscopic cutting instrument of FIG. 28. A portion of the disc annulus may be removed to form an access channel or an incision may be created and the incision edges spread open through the tissue spreading element deployed by the instrument of FIG. 1. Alternatively, the disc annulus may be incised using a laser or an access port created using a trephine.

The endoscopic cutting instrument of FIG. 28 is inserted into the disc nucleus. Following insertion into the disc nucleus and extension of the knife blade, the cutting instrument slices away portions of the disc nucleus which may be removed using forceps, rongeurs, or suction instruments. Other instruments may be selected for disc removal including lasers, rongeurs, shavers, and the like. Using the anterior approach, as much or as little of the herniated nucleus may be removed as needed to alleviate compression of adjacent muscles and nerves. This surgical procedure permits the surgeon to directly monitor the disc removal process by means of an endoscope.

The instruments described above are preferably composed of relatively inexpensive materials so that they are single-use disposable instruments which can be discarded after use. However, it is also contemplated that they can be re-usable or semi-reusable in that a portion of the instrument is re-sterilized, e.g. the hand, and the remaining portion is disposable, e.g. the jaw structure.

Although the instrumentation of the present invention has been described for use in endoscopic discectomy procedures, the instruments can be used for facilitating other endoscopic (minimally invasive) surgical procedures. These include, for example, spreading the vertebrae to aid spinal fusion. Spinal fusion is used to stabilize spinal segments and is currently performed using fusion baskets, bone plugs or other internal fixation devices.

While the invention has been particularly shown and described with reference to the preferred embodiments, it will be understood by those skilled in the art that various modifications and changes in form and detail may be made without departing from the scope and spirit of the invention. Accordingly, modifications such as those suggested above, but not limited thereto, are to be considered within the scope of the invention.

What is claimed is:

1. An endoscopic surgical instrument for spreading vertebrae comprising:

a handle portion including a manually operable member;

an elongated endoscopic portion connected to said handle portion and extending distally therefrom, said endoscopic portion defining a longitudinal axis and having proximal and distal end portions;

a vertebrae spreading mechanism movably mounted with respect to said endoscopic portion, said vertebrae spreading mechanism including first and second vertebrae spreading arm members;

an actuation mechanism at least partially housed within said endoscopic portion and movable in response to movement of said manually operable member, said actuation mechanism including at least one camming element engageable with said first and second arm members to move said arm members from a closed to an open position, said first and second arm members deployable in a general transverse direction with respect to said longitudinal axis in response to movement of said manually operable member such that said first and second arm members remain in general parallel relation during deployment.

2. An endoscopic surgical instrument according to claim 1 wherein said actuation mechanism includes a rod member coaxially mounted within said endoscopic portion and reciprocally movable therewithin, said at least one camming element being positioned at a distal end of said rod member.

3. An endoscopic surgical instrument according to claim 2 wherein said first and second vertebrae spreading arm members include camming surfaces on an interior surface thereof, said camming surfaces configured to interfit with said at least one camming element.

4. An endoscopic surgical instrument according to claim 2 wherein said first and second vertebrae spreading arm members include substantially planar tissue contacting surfaces.

5. An endoscopic surgical instrument according to claim 4, wherein said tissue contacting surfaces of said first and second vertebrae spreading arm members extend in first and second planes respectively, said first and second planes being in general parallel relation to each other when the vertebrae spreading mechanism is in said closed position;

wherein during deployment of said vertebrae spreading mechanism said first and second planes remain substantially mutually parallel between said closed and open positions.

6. An endoscopic surgical instrument according to claim 5 wherein said first and second arm members include camming surfaces on interior surfaces thereof, said camming surfaces configured to interfit with said at least one camming element for movement of said arm members between said closed and open positions.

7. An endoscopic surgical instrument according to claim 1 wherein said first and second vertebrae spreading arm members include curved tissue contacting surfaces.

8. An endoscopic surgical instrument according to claim 1 wherein said vertebrae spreading arm members include means for enhancing engagement with tissue.

9. An endoscopic surgical instrument according to claim 8 wherein said means for enhancing engagement is in the form of ridges, knurling, and serrations.

10. An endoscopic surgical instrument for spreading vertebrae, which comprises:
   an elongated frame defining a longitudinal axis and having proximal and distal end portions;
   at least first and second vertebrae spreading arm members mounted to the distal end portion of the elongated frame, the first and second arm members moveable between a closed approximated position and an open spread position, and defining first and second outer tissue contacting surfaces, the first and second tissue contacting surfaces being in substantial parallel relation during movement of the first and second arm members between the closed and open positions and having structure to facilitate engagement with the vertebrae; and
   camming means operatively engageable with the first and second arm members and actuable to move the spreading arm members between the closed and open positions.

11. The surgical instrument according to claim 10 wherein the camming means is actuable by a proximally positioned manually operable member.

12. The surgical instrument according to claim 11 including an actuating rod operatively connected to the manually operable member, the actuating rod moveable in response to corresponding movement of the manually operable member to actuate the camming means to thereby move the arm members between the closed and open positions.

13. The surgical instrument according to claim 12 wherein the manually operable member is adapted for rotational movement.

14. The surgical instrument according to claim 12 wherein the structure of the tissue contacting surfaces are in the form of ridges, knurling or serrations.

15. The surgical instrument according to claim 12 wherein the first and second tissue contacting surfaces are substantially planar.

16. The surgical instrument according to claim 15 wherein the first and second tissue contacting surfaces are in general parallel relation with the longitudinal axis of the frame during movement of the first and second arm members between the closed and open positions.

17. An endoscopic surgical instrument for distracting vertebrae, which comprises:
   an elongated frame defining a central longitudinal axis and having proximal and distal end portions;
   at least two vertebrae spreading members mounted to the distal end portion of the elongated frame, at least one spreading member adapted for displacing movement relative to the other spreading member between a closed approximated position and an open spread position, the spreading members defining outer tissue contacting surfaces having structure to enhance engagement with the vertebrae, the tissue contacting surfaces being equidistally spaced with respect to the central longitudinal axis when in the open spread position;
   a camming mechanism operatively engageable with the spreading members and having at least one camming element, the camming element moveable to move the spreading members between the closed and open positions; and
   a proximally positioned manually operable member for actuating the camming mechanism.

18. The surgical instrument according to claim 17 wherein each vertebrae spreading member is adapted for movement in a general transverse direction relative to the central longitudinal axis between the closed and open positions.

19. The surgical instrument according to claim 18 wherein the tissue contacting surfaces are configured and dimensioned to be equidistally spaced with respect to the central longitudinal axis during movement between the closed and open positions.

20. The surgical instrument according to claim 19 wherein the tissue contacting surfaces are curved.

21. The surgical instrument according to claim 19 wherein the tissue contacting surfaces are planar.

22. An endoscopic surgical instrument for spreading vertebrae, which comprises:
   a handle portion having a manually operable actuating member;
   an endoscopic portion connected to the handle portion and extending distally therefrom, the endoscopic portion including:
      an outer sleeve defining a longitudinal axis and having proximal and distal end portions; and
      an actuating rod disposed within the outer sleeve and reciprocally movable therein in response to movement of the manually operable member;
   at least a pair of vertebrae spreading members mounted to the distal end portion of the outer sleeve, the vertebrae spreading members extending in a general longitudinal direction and being in general parallel relation with the central longitudinal axis, the vertebrae spreading members adapted for relative movement to be displaced in a general transverse direction relative to the longitudinal axis while maintaining their parallel relation, the spreading members having outer contacting surfaces with structure to enhance engagement with the vertebrae; and
   a camming mechanism including at least one camming element operatively engageable with the vertebrae spreading members and actuable in response to movement of the actuating rod to move the spreading members between a generally closed approximated position and an open spread position.

23. The surgical instrument according to claim 22 wherein the outer contacting surfaces of the spreading members are arcuate.

24. The surgical instrument according to claim 22 wherein the outer contacting surfaces of the spreading members are substantially planar.

* * * * *